US006372212B1

(12) United States Patent
Gray

(10) Patent No.: US 6,372,212 B1
(45) Date of Patent: *Apr. 16, 2002

(54) CHITINASE MATERIALS AND METHODS

(75) Inventor: Patrick W. Gray, Seattle, WA (US)

(73) Assignee: ICOS Corporation, Bothell, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/877,599

(22) Filed: Jun. 16, 1997

Related U.S. Application Data

(63) Continuation-in-part of application No. 08/663,618, filed on Jun. 14, 1996.

(51) Int. Cl.[7] ............ C12N 9/42; C12N 15/56; A61K 38/47
(52) U.S. Cl. ............ 424/94.61; 435/209; 536/23.2
(58) Field of Search ............ 424/94.61; 435/209; 536/23.2

(56) References Cited

U.S. PATENT DOCUMENTS

| | | | |
|---|---|---|---|
| 5,326,561 A | 7/1994 | Harman et al. | 424/94.61 |
| 5,433,947 A | 7/1995 | Harman et al. | 424/94.61 |
| 5,928,928 A | 7/1999 | Aerts | 435/201 |
| 6,057,142 A | 5/2000 | Aerts | 435/209 |

FOREIGN PATENT DOCUMENTS

| | | |
|---|---|---|
| WO | 95/34678 | 12/1995 |
| WO | 96/40940 | 12/1996 |
| WO | 97/36917 | 10/1997 |

OTHER PUBLICATIONS

A.M. Pope et al. "The Influence of Carbohydrases on the Growth of Fungal Pathogens In vitro and In vivo", Medline Accession No. 80101245 citing Postgraduate Med. J. 55 (647): 674–646, Sep. 1979.*
D.A.L. Davies et al. "Mycolase, a New Kind of Systemic Antimycotic", Nature 273: 235–236, May 1978.*
G.H. Renkema et al., "Purification and Characterization of Human Chitotriosidase, a Novel Member of the Chitinase Family of Proteins", J. Biol. Chem. 270 (5): 2198–2202, Feb. 1995.*
R.G. Bootet al., "Cloning of a cDNA Ecoding Chitotriosidase, a Human Chitinase Produced by Macrophages", J. Biol. Chem. 270 (44): 26252–26256, Nov. 1995.*
Altschul et al., "Basic Local Alignment Search Tool," J. Mol. Biol., 215:403–410 (1990).
Andriole et al., "Animal Models: Usefulness for Studies of Fungal Pathogenesis and Drug Efficacy in Aspergillosis," Clin. Infect. Dis., 14(Suppl 1):S134–S138 (1992).

Argueso et al., "Effect of the Enzymes Chitinase and Neuraminidase on the Structure of Human Ocular Mucus," Investigative Ophthalmology & Visual Science, 36(4):S997 (Mar. 15, 1995) (Abstract 4615–596).
Bayer et al., "Experimental Intraabdominal Candidiasis in Rabbits: Therapy with Low–Total–Dose Intravenous Amphotericin B," Antimicrobiol Agents Chemotherapy, 19(1):179–184 (Jan., 1981).
Bitter et al., "Secretion of Foreign Proteins from Saccharomyces cerevisiae Directed by α–Factor Gene Fusions," Proc. Natl. Acad. Sci. USA, 81:5330–5334 (1984).
Boot et al., "Cloning of cDNA Encoding Chitotriosidase, A Human Chitinase Produced by Macrophage," J. Biol. Chem., 270(44):26252–26256 (Nov. 3, 1995).
Capecchi, "Altering the Genome by Homologous Recombination," Science, 244: 1288–1292 (1989).
Chilvers et al., "Bronchoalveolar lavage in an immunosuppressed rabbit model of invasive pulmonary aspergillosis," Mycopathologia, 108:163–71 (1989).
Clark–Lewis et al., "Automated Chemical Synthesis of a Protein Growth Factor for Hemopoietic Cells, Interleukin–3," Science, 231:134–139 (Jan. 10, 1986).
Clark–Lewis et al., "Structure–Activity Relationships of Interleukin–8 Determined Using Chemically Synthesized Analogs," J. Biol Chem., 266:23128–23134 (1991).
Clarke et al., "The nucleotide sequence of the araC regulatory gene in Salmonella typhimurim LT2," Gene 18:157–163 (1982).
Dawson et al., "Synthesis of Proteins by Native Chemical Ligation," Science, 266:776–779 (Nov. 4, 1994).
DeSouza et al., "An Estrogen–Dependent Secretory Protein, which Shares Identity with Chitinases, Is Expressed in a Temporally and Regionally Specific Manner in the Sheep Oviduct at the Time of Fertilization and Embryo Development," Endocrinology, 136:2485–2496 (1995).
Escott et al., "Chitinase Activity in Human Serum and Leukocytes," Infect. Immun., 63(12):4770–4773 (Dec., 1995).
Falcone et al., "Analysis of a 1.6μm Circular Plasmid from the Yeast Kluyveromyces drosophilarum: Structure and Molecular Dimorphism," Plasmid, 15:248–252 (1986).
Feldmann et al., "Rheumatoid Arthritis," Cell, 85:307–310 (May 3, 1996).
Genbank report for accession No. U14639. Apr. 1996.
Genbank report for Accession No. Z36295. Feb. 1995.
Genbank report for accession no. X77111. Jun. 1994.

(List continued on next page.)

Primary Examiner—Rebecca E. Prouty
(74) Attorney, Agent, or Firm—Marshall, Gerstein & Borun

(57) ABSTRACT

The present invention provides purified and isolated polynucleotide sequences encoding human chitinase. Also provided are materials and methods for the recombinant production of human chitinase products which are expected to be useful as products for treating fungal infections or for development of products useful for treating the same.

8 Claims, No Drawings

OTHER PUBLICATIONS

Genbank report for Accession No. U10422. Jan. 1995.

Genbank report for Accession No. M94584. Jun. 1992.

George et al., "Combination Therapy in Experimental Invasive Aspergillosis," *J. Infect. Dis.*, 168:692–698 (1993).

Georgopapadakou et al., "The Fungal Cell Wall As a Drug Target," *Trends in Microbiology*, 3(3):98–104 (Mar., 1995).

Gillis et al., "Production of Recombinant Human Colony Stimulating Factors in Yeast," *Behring Inst. Mitt.*, No. 83:1–7 (1988).

Hakala et al., "Human Cartilage gp–39, A Major Secretory Product of Articular Chondrocytes and Synovial Cells, Is a Mammalian Member of a Chitinase Protein Family," *J. Biol. Chem.*, 268(34):25803–25810 (Dec. 5, 1993).

Heitz et al., "Molecular Characterization of a Novel Tobacco Pathogenesis–Related (PR) Protein: A New Plant Chitinase/Lysozyme," *Mol. Gen. Genet.*, 245:246–254 (1994).

Hollak et al., "Marked Elevation of Plasma Chitotriosidase Activity: A Novel Hallmark of Gaucher Disease," *J. Clin. Invest.*, 93:1288–1292 (Mar., 1994).

Jain et al., "Electroretinograms in early fungal endophthalmitis," *Doc. Ophthalmol.*, 69:227–235 (1988).

Johansen et al., "Serum YKL–40: A New Potential Marker of Prognosis and Location of Metastases of Patients With Recurrent Breast Cancer," *Eur. J. Cancer*, 31A(9):1437–1442 (1995).

Jones et al., "Isolation and Characterization of Genes Encoding Two Chitinase Enzymes from *Serratia marcescens*," *EMBO J.*, 5(3):467–473 (1986).

Kinsman et al., "Antifungal Properties in a Novel Series of Triazino [5,6–b] Indoles," *Antimicrobial Agents Chemotherapy*, 37(6):1243–1246 (Jun., 1993).

Krishnan et al., "Isolation, Cloning, and Characterization of New Chitinase Stored in Active Form in Chitin–lined Venom Reservoir," *J. Biol. Chem.*, 269(33):20971–20976 (Aug. 19, 1994).

Kurjan and Herskowitz, "Structure of a Yeast Pheromone Gene (MFα): A Putative α–Factor Precursor Contains Four Tandem Copies of Mature α–Factor," *Cell*, 30:933–943 (1982).

Lin et al., "The araBAD operon of *Salmonella typhimurium* LT2 II. Nucleotide sequence of araA and primary structure of its product, L–arabinose isomerase," *Gene* 34:123–128 (1985).

Longman et al., "Efficacy of Fluconazole in Prophylaxis and Treatment of Experimental Candida Endocarditis," *Rev. Infect. Dis.*, 12(Suppl. 3):S294–298 (1990).

Louie et al., "Tumor Necrosis Factor Alpha Has a Protective Role in a Murine Model of Systemic Candidiasis," *Infect. Immun.*, 62(7):2761–2772 (Jul., 1994).

Nakajima et al., "In Vitro and In Vivo Antifungal Activities of DU–6859a, a Fluoroquinolone, in Combination with Amphotericin B and Fluconazole Against Pathogenic Fungi," *Antimicrobial Agents Chemotherapy*, 39(7):1517–1521 (Jul., 1995).

Orr–Weaver et al., "Yeast transformation: A model system for the study of recombination," *Proc. Natl. Acad. Sci, USA*, 78:6354–6358 (1981).

Overdijk et al., "Human Serum Contains a Chitinase: Identification of an Enzyme, Formerly Described as 4–Methylumbelliferyl–tetra–N–Acetylchitotetraoside Hydrolase (MU–TACT Hydrolase)," *Glycobiology*, 4(6):797–803 (1994).

Park et al., "Treatment of Exogenous Candida Endophthalmitis in Rabbits with Oral Fluconazole," *Antimicrobial Agents Chemotherapy*, 39(4):958–963 (Apr., 1995).

Patterson et al., "Efficacy of Itraconazole Solution in a Rabbit Model of Invasive Aspergillosis," *Antimicrobial Agents Chemotherapy*, 37(11):2307–2310 (Nov., 1993).

Price et al., "Expression, Purification and Characterization of Recombinant Murine Granulocyte–Macrophage Colony––Stimulating Factor and Bovine Interleukins–2 From Yeast," *Gene*, 55:287–293 (1987).

Recklies et al., "Expression of a Chitinase–like Protein (C–GP39) in Human Articular Cartilage and Synovium," *Arthritis Rheumatism*, 36(9 Suppl.):S190 (1993) (Abstract C15).

Renkema et al., "Purification and Characterization of Human Chitotriosidase, a Novel Member of the Chitinase Family of Proteins," *J. Biol. Chem.*, 270(5):2198–2202 (Feb. 3, 1995).

Rose and Broach, "Propagation and Expression of Cloned Genes in Yeast: 2–μm Circle–Based Vectors," *Meth. Enz.*, 185:234–279, D. Goeddel, ed., Academic Press, Inc., San Diego, CA (1990).

Rouse et al., "Efficacy of Cilofungin Therapy Administered by Continuous Intravenous Infusion for Experimental Disseminated Candidiasis in Rabbits," *Antimicrobial Agents Chemotherapy*, 36(1):56–58 (Jan., 1992).

Semino et al., "Homologs of the Xenopus Developmental Gene DG42 are Present in Zebrafish and Mouse and are Involved in the Synthesis of Nod–like Chitin Oligosaccharides During Early Embryogenesis," *Proc. Nat'l Acad. Sci., USA*, 93:4548–4553 (May, 1996).

Sleep et al., "The Secretion of Human Serum Albumin from the Yeast *Saccharomyces cerevisiae* Using Five Different Leader Sequences," *Bio/Technol.*, 8:42–46 (1990).

Spitz, "Single–Shot Intrasplenic Immunization of the Production of Monoclonal Antibodies," *Methods Enz.*, 121:33–41 (1986).

Stearns et al., "Manipulating Yeast Genome Using Plasmid Vectors," *Meth. Enz.*, 185:280–297, Goeddel et al., (ed), Academic Press, Inc., San Diego, CA,.

Tjoelker et al., "Anti–flammatory Properties of a Platelet–activating Factor Acetylhydrolase," *Nature*, 374:549–553 (1995).

Tonnetti et al., "Interleukin–4 and –10 Exacerbate Candidiasis in Mice," *Eur. J. Immunol.*, 25:1559–1565 (1995).

Varki, A., "Does DG42 Synthesize Hyaluronan or Chitin?:A Controversy About Oligosaccharides in Vertebrate Development," *Proc. Nat'l Acad. Sci., USA*, 93:4523–4525 (May, 1996).

Witt et al., "Comparison of Fluconazole and Amphotericin B for Prevention and Treatment of Experimental Candida Endocarditis," *Antimicrobial Agents Chemotherapy*, 35(12):2481–2485 (Dec., 1991).

Davies et al., "Mycolase, a new kind of systemic antimycotic," *Nature* 273:235–236 (May 1978).

Denning et al., "Efficacy of Cilofungin Alone and in Combination with Amphotericin B in a Murine Model of Disseminated Aspergillosis," *Antimicrobial Agents Chemotherapy*, 35(7):1329–1333 (Jul. 1991).

Selitrennikoff, C., "Use of a Temperature–Sensitive, Protoplast–Forming *Neurospora crassa* Strain for the Detection of Antifungal Antibiotics," *Antimicrobial Agents Chemotherapy*, 23(5):757–765 (May 1983).

Stevens, D., "Animal Models in the Evaluation of Antifungal Drugs," *J. Mycol. Med.*, 6 (Suppl. I):7–10 (1996).

Henrissat et al., "New families in the classification of glycosyl hydrolases based on amino acid sequence similarities," *Biochem.J.*, 293:781–788 (1993).

Renkema et al., "Synthesis, sorting, and processing into distinct isoforms of human macrophage chitotriosidase," *Eur. J. Biochem.*, 244(2):279–285 (1997).

McGinnis and Rinaldi, "Antifungal Drugs: Mechanisms of Action, Drug Resistance, Susceptibility Testing, and Assays of Activity in Biologic Fluids," Chapter 5, *Antibiotics in Laboratory Medicine*, 4th ed., Williams & Wilkins, Baltimore (1996).

Pope and Davies, "The influence of carbohydrases on the growth of fungal pathogens." *Postgraduate Medical J.*, 55:674–676 (1979).

Rex et al., "Development of Interpretive Breakpoints for Antifungal Susceptibility Testing: Conceptual Framework and Analysis of In Vitro–In Vivo Correlation Data for Fluconazole, Itraconazole, and Candida Infections," *Clin. Infect. Dis.*, 24:235–247 (1997).

09/409,918 Allison et al.

* cited by examiner

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 1636 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 2..1399

(ix) FEATURE:
      (A) NAME/KEY: mat_peptide
      (B) LOCATION: 65..1399

(xi) SEQUENCE DESCRIPTION: SEQ ID NO: 1:

```
C ATG GTG CGG TCT GTG GCC TGG GCA GGT TTC ATG GTC CTG CTG ATG        46
  Met Val Arg Ser Val Ala Trp Ala Gly Phe Met Val Leu Leu Met
  -21 -20              -15                 -10

ATC CCA TGG GGC TCT GCT GCA AAA CTG GTC TGC TAC TTC ACC AAC TGG      94
Ile Pro Trp Gly Ser Ala Ala Lys Leu Val Cys Tyr Phe Thr Asn Trp
    -5              1               5                  10
```

-continued

```
GCC CAG TAC AGA CAG GGG GAG GCT CGC TTC CTG CCC AAG GAC TTG GAC        142
Ala Gln Tyr Arg Gln Gly Glu Ala Arg Phe Leu Pro Lys Asp Leu Asp
             15                  20                  25

CCC AGC CTT TGC ACC CAC CTC ATC TAC GCC TTC GCT GGC ATG ACC AAC        190
Pro Ser Leu Cys Thr His Leu Ile Tyr Ala Phe Ala Gly Met Thr Asn
         30                  35                  40

CAC CAG CTG AGC ACC ACT GAG TGG AAT GAC GAG ACT CTC TAC CAG GAG        238
His Gln Leu Ser Thr Thr Glu Trp Asn Asp Glu Thr Leu Tyr Gln Glu
             45                  50                  55

TTC AAT GGC CTG AAG AAG ATG AAT CCC AAG CTG AAG ACC CTG TTA GCC        286
Phe Asn Gly Leu Lys Lys Met Asn Pro Lys Leu Lys Thr Leu Leu Ala
         60                  65                  70

ATC GGA GGC TGG AAT TTC GGC ACT CAG AAG TTC ACA GAT ATG GTA GCC        334
Ile Gly Gly Trp Asn Phe Gly Thr Gln Lys Phe Thr Asp Met Val Ala
 75                  80                  85                  90

ACG GCC AAC AAC CGT CAG ACC TTT GTC AAC TCG GCC ATC AGG TTT CTG        382
Thr Ala Asn Asn Arg Gln Thr Phe Val Asn Ser Ala Ile Arg Phe Leu
                 95                 100                 105

CGC AAA TAC AGC TTT GAC GGC CTT GAC CTT GAC TGG GAG TAC CCA GGA        430
Arg Lys Tyr Ser Phe Asp Gly Leu Asp Leu Asp Trp Glu Tyr Pro Gly
             110                 115                 120

AGC CAG GGG AGC CCT GCC GTA GAC AAG GAG CGC TTC ACA ACC CTG GTA        478
Ser Gln Gly Ser Pro Ala Val Asp Lys Glu Arg Phe Thr Thr Leu Val
         125                 130                 135

CAG GAC TTG GCC AAT GCC TTC CAG CAG GAA GCC CAG ACC TCA GGG AAG        526
Gln Asp Leu Ala Asn Ala Phe Gln Gln Glu Ala Gln Thr Ser Gly Lys
     140                 145                 150

GAA CGC CTT CTT CTG AGT GCA GCG GTT CCA GCT GGG CAG ACC TAT GTG        574
Glu Arg Leu Leu Leu Ser Ala Ala Val Pro Ala Gly Gln Thr Tyr Val
155                 160                 165                 170

GAT GCT GGA TAC GAG GTG GAC AAA ATC GCC CAG AAC CTG GAT TTT GTC        622
Asp Ala Gly Tyr Glu Val Asp Lys Ile Ala Gln Asn Leu Asp Phe Val
                 175                 180                 185

AAC CTT ATG GCC TAC GAC TTC CAT GGC TCT TGG GAG AAG GTC ACG GGA        670
Asn Leu Met Ala Tyr Asp Phe His Gly Ser Trp Glu Lys Val Thr Gly
             190                 195                 200

CAT AAC AGC CCC CTC TAC AAG AGG CAA GAA GAG AGT GGT GCA GCA GCC        718
His Asn Ser Pro Leu Tyr Lys Arg Gln Glu Glu Ser Gly Ala Ala Ala
         205                 210                 215

AGC CTC AAC GTG GAT GCT GCT GTG CAA CAG TGG CTG CAG AAG GGG ACC        766
Ser Leu Asn Val Asp Ala Ala Val Gln Gln Trp Leu Gln Lys Gly Thr
     220                 225                 230

CCT GCC AGC AAG CTG ATC CTT GGC ATG CCT ACC TAC GGA CGC TCC TTC        814
Pro Ala Ser Lys Leu Ile Leu Gly Met Pro Thr Tyr Gly Arg Ser Phe
235                 240                 245                 250

ACA CTG GCC TCC TCA TCA GAC ACC AGA GTG GGG GCC CCA GCC ACA GGG        862
Thr Leu Ala Ser Ser Ser Asp Thr Arg Val Gly Ala Pro Ala Thr Gly
                 255                 260                 265

TCT GGC ACT CCA GGC CCC TTC ACC AAG GAA GGA GGG ATG CTG GCC TAC        910
Ser Gly Thr Pro Gly Pro Phe Thr Lys Glu Gly Gly Met Leu Ala Tyr
             270                 275                 280

TAT GAA GTC TGC TCC TGG AAG GGG GCC ACC AAA CAG AGA ATC CAG GAT        958
Tyr Glu Val Cys Ser Trp Lys Gly Ala Thr Lys Gln Arg Ile Gln Asp
         285                 290                 295

CAG AAG GTG CCC TAC ATC TTC CGG GAC AAC CAG TGG GTG GGC TTT GAT       1006
Gln Lys Val Pro Tyr Ile Phe Arg Asp Asn Gln Trp Val Gly Phe Asp
     300                 305                 310

GAT GTG GAG AGC TTC AAA ACC AAG GTC AGC TAT CTG AAG CAG AAG GGA       1054
Asp Val Glu Ser Phe Lys Thr Lys Val Ser Tyr Leu Lys Gln Lys Gly
315                 320                 325                 330
```

-continued

```
CTG GGC GGG GCC ATG GTC TGG GCA CTG GAC TTA GAT GAC TTT GCC GGC        1102
Leu Gly Gly Ala Met Val Trp Ala Leu Asp Leu Asp Asp Phe Ala Gly
            335                 340                 345

TTC TCC TGC AAC CAG GGC CGA TAC CCC CTC ATC CAG ACG CTA CGG CAG        1150
Phe Ser Cys Asn Gln Gly Arg Tyr Pro Leu Ile Gln Thr Leu Arg Gln
            350                 355                 360

GAA CTG AGT CTT CCA TAC TTG CCT TCA GGC ACC CCA GAG CTT GAA GTT        1198
Glu Leu Ser Leu Pro Tyr Leu Pro Ser Gly Thr Pro Glu Leu Glu Val
            365                 370                 375

CCA AAA CCA GGT CAG CCC TCT GAA CCT GAG CAT GGC CCC AGC CCT GGA        1246
Pro Lys Pro Gly Gln Pro Ser Glu Pro Glu His Gly Pro Ser Pro Gly
380                 385                 390

CAA GAC ACG TTC TGC CAG GGC AAA GCT GAT GGG CTC TAT CCC AAT CCT        1294
Gln Asp Thr Phe Cys Gln Gly Lys Ala Asp Gly Leu Tyr Pro Asn Pro
395                 400                 405                 410

CGG GAA CGG TCC AGC TTC TAC AGC TGT GCA GCG GGG CGG CTG TTC CAG        1342
Arg Glu Arg Ser Ser Phe Tyr Ser Cys Ala Ala Gly Arg Leu Phe Gln
            415                 420                 425

CAA AGC TGC CCG ACA GGC CTG GTG TTC AGC AAC TCC TGC AAA TGC TGC        1390
Gln Ser Cys Pro Thr Gly Leu Val Phe Ser Asn Ser Cys Lys Cys Cys
            430                 435                 440

ACC TGG AAT TGAGTCGCTA AAGCCCCTCC AGTCCCAGCT TTGAGGCTGG                1439
Thr Trp Asn
        445

GCCCAGGATC ACTCTACAGC CTGCCTCCTG GGTTTTCCCT GGGGGCCGCA ATCTGGCTCC      1499

TGCAGGCCTT TCTGTGGTCT TCCTTTATCC AGGCTTTCTG CTCTCAGCCT TGCCTTCCTT      1559

TTTTCTGGGT CTCCTGGGCT GCCCCTTTCA CTTGCAAAAT AAATCTTTGG TTTGTGCCCC      1619

TCTTCCCAAA AAAAAA                                                      1636
```

(2) INFORMATION FOR SEQ ID NO: 2:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Val Arg Ser Val Ala Trp Ala Gly Phe Met Val Leu Leu Met Ile
-21 -20                 -15                 -10

Pro Trp Gly Ser Ala Ala Lys Leu Val Cys Tyr Phe Thr Asn Trp Ala
-5                  1                   5                   10

Gln Tyr Arg Gln Gly Glu Ala Arg Phe Leu Pro Lys Asp Leu Asp Pro
            15                  20                  25

Ser Leu Cys Thr His Leu Ile Tyr Ala Phe Ala Gly Met Thr Asn His
            30                  35                  40

Gln Leu Ser Thr Thr Glu Trp Asn Asp Glu Thr Leu Tyr Gln Glu Phe
    45                  50                  55

Asn Gly Leu Lys Lys Met Asn Pro Lys Leu Lys Thr Leu Leu Ala Ile
60                  65                  70                  75

Gly Gly Trp Asn Phe Gly Thr Gln Lys Phe Thr Asp Met Val Ala Thr
                80                  85                  90

Ala Asn Asn Arg Gln Thr Phe Val Asn Ser Ala Ile Arg Phe Leu Arg
            95                  100                 105

Lys Tyr Ser Phe Asp Gly Leu Asp Leu Asp Trp Glu Tyr Pro Gly Ser
        110                 115                 120
```

```
Gln Gly Ser Pro Ala Val Asp Lys Glu Arg Phe Thr Thr Leu Val Gln
    125                 130                 135

Asp Leu Ala Asn Ala Phe Gln Gln Ala Gln Thr Ser Gly Lys Glu
140                 145                 150                 155

Arg Leu Leu Leu Ser Ala Ala Val Pro Ala Gly Gln Thr Tyr Val Asp
                160                 165                 170

Ala Gly Tyr Glu Val Asp Lys Ile Ala Gln Asn Leu Asp Phe Val Asn
            175                 180                 185

Leu Met Ala Tyr Asp Phe His Gly Ser Trp Glu Lys Val Thr Gly His
        190                 195                 200

Asn Ser Pro Leu Tyr Lys Arg Gln Glu Glu Ser Gly Ala Ala Ala Ser
    205                 210                 215

Leu Asn Val Asp Ala Ala Val Gln Gln Trp Leu Gln Lys Gly Thr Pro
220                 225                 230                 235

Ala Ser Lys Leu Ile Leu Gly Met Pro Thr Tyr Gly Arg Ser Phe Thr
                240                 245                 250

Leu Ala Ser Ser Ser Asp Thr Arg Val Gly Ala Pro Ala Thr Gly Ser
            255                 260                 265

Gly Thr Pro Gly Pro Phe Thr Lys Glu Gly Met Leu Ala Tyr Tyr
        270                 275                 280

Glu Val Cys Ser Trp Lys Gly Ala Thr Lys Gln Arg Ile Gln Asp Gln
    285                 290                 295

Lys Val Pro Tyr Ile Phe Arg Asp Asn Gln Trp Val Gly Phe Asp Asp
300                 305                 310                 315

Val Glu Ser Phe Lys Thr Lys Val Ser Tyr Leu Lys Gln Lys Gly Leu
                320                 325                 330

Gly Gly Ala Met Val Trp Ala Leu Asp Leu Asp Asp Phe Ala Gly Phe
            335                 340                 345

Ser Cys Asn Gln Gly Arg Tyr Pro Leu Ile Gln Thr Leu Arg Gln Glu
    350                 355                 360

Leu Ser Leu Pro Tyr Leu Pro Ser Gly Thr Pro Glu Leu Glu Val Pro
365                 370                 375

Lys Pro Gly Gln Pro Ser Glu Pro Glu His Gly Pro Ser Pro Gly Gln
380                 385                 390                 395

Asp Thr Phe Cys Gln Gly Lys Ala Asp Gly Leu Tyr Pro Asn Pro Arg
                400                 405                 410

Glu Arg Ser Ser Phe Tyr Ser Cys Ala Ala Gly Arg Leu Phe Gln Gln
            415                 420                 425

Ser Cys Pro Thr Gly Leu Val Phe Ser Asn Ser Cys Lys Cys Thr
    430                 435                 440

Trp Asn
    445

(2) INFORMATION FOR SEQ ID NO: 3:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 27..1424
```

-continued (ix) FEATURE:
    (A) NAME/KEY: mat_peptide
    (B) LOCATION: 90..1424

(xi) SEQUENCE DESCRIPTION: SEQ ID NO: 3:

| | | | | | | | | | | | | | | | |
|---|---|---|---|---|---|---|---|---|---|---|---|---|---|---|---|
| GCTGCAGCCT | GCCGCTGAGC | TGCATC | ATG | GTG | CGG | TCT | GTG | GCC | TGG | GCA | GGT | | | | 53 |
| | | | Met | Val | Arg | Ser | Val | Ala | Trp | Ala | Gly | | | | |
| | | | -21 | -20 | | | | -15 | | | | | | | |

```
TTC ATG GTC CTG CTG ATG ATC CCA TGG GGC TCT GCT GCA AAA CTG GTC           101
Phe Met Val Leu Leu Met Ile Pro Trp Gly Ser Ala Ala Lys Leu Val
        -10             -5                    1

TGC TAC TTC ACC AAC TGG GCC CAG TAC AGA CAG GGG GAG GCT CGC TTC           149
Cys Tyr Phe Thr Asn Trp Ala Gln Tyr Arg Gln Gly Glu Ala Arg Phe
  5              10                  15                  20

CTG CCC AAG GAC TTG GAC CCC AGC CTT TGC ACC CAC CTC ATC TAC GCC           197
Leu Pro Lys Asp Leu Asp Pro Ser Leu Cys Thr His Leu Ile Tyr Ala
                25                  30                  35

TTC GCT GGC ATG ACC AAC CAC CAG CTG AGC ACC ACT GAG TGG AAT GAC           245
Phe Ala Gly Met Thr Asn His Gln Leu Ser Thr Thr Glu Trp Asn Asp
            40                  45                  50

GAG ACT CTC TAC CAG GAG TTC AAT GGC CTG AAG AAG ATG AAT CCC AAG           293
Glu Thr Leu Tyr Gln Glu Phe Asn Gly Leu Lys Lys Met Asn Pro Lys
        55                  60                  65

CTG AAG ACC CTG TTA GCC ATC GGA GGC TGG AAT TTC AGC ACT CAG AAG           341
Leu Lys Thr Leu Leu Ala Ile Gly Gly Trp Asn Phe Ser Thr Gln Lys
    70                  75                  80

TTC ACA GAT ATG GTA GCC ACG GCC AAC AAC CGT CAG ACC TTT GTC AAC           389
Phe Thr Asp Met Val Ala Thr Ala Asn Asn Arg Gln Thr Phe Val Asn
 85                  90                  95                 100

TCG GCC ATC AGG TTT CTG CGC AAA TAC AGC TTT GAC GGC CTT GAC CTT           437
Ser Ala Ile Arg Phe Leu Arg Lys Tyr Ser Phe Asp Gly Leu Asp Leu
                105                 110                 115

GAC TGG GAG TAC CCA GGA AGC CAG GGG AGC CCT GCC GTA GAC AAG GAG           485
Asp Trp Glu Tyr Pro Gly Ser Gln Gly Ser Pro Ala Val Asp Lys Glu
            120                 125                 130

CGC TTC ACA ACC CTG GTA CAG GAC TTG GCC AAT GCC TTC CAG CAG GAA           533
Arg Phe Thr Thr Leu Val Gln Asp Leu Ala Asn Ala Phe Gln Gln Glu
        135                 140                 145

GCC CAG ACC TCA GGG AAG GAA CGC CTT CTT CTG AGT GCA GCG GTT CCA           581
Ala Gln Thr Ser Gly Lys Glu Arg Leu Leu Leu Ser Ala Ala Val Pro
    150                 155                 160

GCT GGG CAG ACC TAT GTG GAT GCT GGA TAC GAG GTG GAC AAA ATC GCC           629
Ala Gly Gln Thr Tyr Val Asp Ala Gly Tyr Glu Val Asp Lys Ile Ala
165                 170                 175                 180

CAG AAC CTG GAT TTT GTC AAC CTT ATG GCC TAC GAC TTC CAT GGC TCT           677
Gln Asn Leu Asp Phe Val Asn Leu Met Ala Tyr Asp Phe His Gly Ser
                185                 190                 195

TGG GAG AAG GTC ACG GGA CAT AAC AGC CCC CTC TAC AAG AGG CAA GAA           725
Trp Glu Lys Val Thr Gly His Asn Ser Pro Leu Tyr Lys Arg Gln Glu
            200                 205                 210

GAG AGT GGT GCA GCA GCC AGC CTC AAC GTG GAT GCT GCT GTG CAA CAG           773
Glu Ser Gly Ala Ala Ala Ser Leu Asn Val Asp Ala Ala Val Gln Gln
        215                 220                 225

TGG CTG CAG AAG GGG ACC CCT GCC AGC AAG CTG ATC CTT GGC ATG CCT           821
Trp Leu Gln Lys Gly Thr Pro Ala Ser Lys Leu Ile Leu Gly Met Pro
    230                 235                 240

ACC TAC GGA CGC TCC TTC ACA CTG GCC TCC TCA TCA GAC ACC AGA GTG           869
Thr Tyr Gly Arg Ser Phe Thr Leu Ala Ser Ser Ser Asp Thr Arg Val
245                 250                 255                 260
```

```
GGG GCC CCA GCC ACA GGG TCT GGC ACT CCA GGC CCC TTC ACC AAG GAA      917
Gly Ala Pro Ala Thr Gly Ser Gly Thr Pro Gly Pro Phe Thr Lys Glu
                265                 270                 275

GGA GGG ATG CTG GCC TAC TAT GAA GTC TGC TCC TGG AAG GGG GCC ACC      965
Gly Gly Met Leu Ala Tyr Tyr Glu Val Cys Ser Trp Lys Gly Ala Thr
            280                 285                 290

AAA CAG AGA ATC CAG GAT CAG AAG GTG CCC TAC ATC TTC CGG GAC AAC     1013
Lys Gln Arg Ile Gln Asp Gln Lys Val Pro Tyr Ile Phe Arg Asp Asn
            295                 300                 305

CAG TGG GTG GGC TTT GAT GAT GTG GAG AGC TTC AAA ACC AAG GTC AGC     1061
Gln Trp Val Gly Phe Asp Asp Val Glu Ser Phe Lys Thr Lys Val Ser
        310                 315                 320

TAT CTG AAG CAG AAG GGA CTG GGG GGG GCC ATG GTC TGG GCA CTG GAC     1109
Tyr Leu Lys Gln Lys Gly Leu Gly Gly Ala Met Val Trp Ala Leu Asp
325                 330                 335                 340

TTA GAT GAC TTT GCC GGC TTC TCC TGC AAC CAG GGC CGA TAC CCC CTC     1157
Leu Asp Asp Phe Ala Gly Phe Ser Cys Asn Gln Gly Arg Tyr Pro Leu
                345                 350                 355

ATC CAG ACG CTA CGG CAG GAA CTG AGT CTT CCA TAC TTG CCT TCA GGC     1205
Ile Gln Thr Leu Arg Gln Glu Leu Ser Leu Pro Tyr Leu Pro Ser Gly
            360                 365                 370

ACC CCA GAG CTT GAA GTT CCA AAA CCA GGT CAG CCC TCT GAA CCT GAG     1253
Thr Pro Glu Leu Glu Val Pro Lys Pro Gly Gln Pro Ser Glu Pro Glu
            375                 380                 385

CAT GGC CCC AGC CCT GGA CAA GAC ACG TTC TGC CAG GGC AAA GCT GAT     1301
His Gly Pro Ser Pro Gly Gln Asp Thr Phe Cys Gln Gly Lys Ala Asp
        390                 395                 400

GGG CTC TAT CCC AAT CCT CGG GAA CGG TCC AGC TTC TAC AGC TGT GCA     1349
Gly Leu Tyr Pro Asn Pro Arg Glu Arg Ser Ser Phe Tyr Ser Cys Ala
405                 410                 415                 420

GCG GGG CGG CTG TTC CAG CAA AGC TGC CCG ACA GGC TTG GTG TTC AGC     1397
Ala Gly Arg Leu Phe Gln Gln Ser Cys Pro Thr Gly Leu Val Phe Ser
                425                 430                 435

AAC TCC TGC AAA TGC TGC ACC TGG AAT TGAGTCGCTA AAGCCCCTCC           1444
Asn Ser Cys Lys Cys Cys Thr Trp Asn
                440             445

AGTCCCAGCT TTGAGGCTGG GCCCAGGATC ACTCTACAGC CTGCCTCCTG GGTTTTCCCT   1504

GGGGGCCGCA ATCGGCTCC  TGCAGGCCTT TCTGTGGTCT TCCTTTATCC AGGCTTTCTG   1564

CTCTCAGCCT TGCCTTCCTT TTTTCTGGGT CTCCTGGGCT GCCCCTTTCA CTTGCAAAAT   1624

AAATCTTTGG TTTGTGCCCC TCAAAAAAAA AA                                 1656

(2) INFORMATION FOR SEQ ID NO: 4:

(i) SEQUENCE CHARACTERISTICS:
        (A) LENGTH: 466 amino acids
        (B) TYPE: amino acid
        (D) TOPOLOGY: linear (ii) MOLECULE TYPE: protein (xi) SEQUENCE DESCRIPTION: SEQ ID NO: 4:

Met Val Arg Ser Val Ala Trp Ala Gly Phe Met Val Leu Leu Met Ile
-21 -20                 -15                 -10

Pro Trp Gly Ser Ala Ala Lys Leu Val Cys Tyr Phe Thr Asn Trp Ala
-5                   1                   5                  10

Gln Tyr Arg Gln Gly Glu Ala Arg Phe Leu Pro Lys Asp Leu Asp Pro
                15                  20                  25

Ser Leu Cys Thr His Leu Ile Tyr Ala Phe Ala Gly Met Thr Asn His
            30                  35                  40
```

```
Gln Leu Ser Thr Thr Glu Trp Asn Asp Glu Thr Leu Tyr Gln Glu Phe
     45                  50                  55

Asn Gly Leu Lys Lys Met Asn Pro Lys Leu Lys Thr Leu Leu Ala Ile
 60                  65                  70                  75

Gly Gly Trp Asn Phe Ser Thr Gln Lys Phe Thr Asp Met Val Ala Thr
                 80                  85                  90

Ala Asn Asn Arg Gln Thr Phe Val Asn Ser Ala Ile Arg Phe Leu Arg
             95                 100                 105

Lys Tyr Ser Phe Asp Gly Leu Asp Leu Asp Trp Glu Tyr Pro Gly Ser
        110                 115                 120

Gln Gly Ser Pro Ala Val Asp Lys Glu Arg Phe Thr Thr Leu Val Gln
    125                 130                 135

Asp Leu Ala Asn Ala Phe Gln Gln Glu Ala Gln Thr Ser Gly Lys Glu
140                 145                 150                 155

Arg Leu Leu Leu Ser Ala Ala Val Pro Ala Gly Gln Thr Tyr Val Asp
                160                 165                 170

Ala Gly Tyr Glu Val Asp Lys Ile Ala Gln Asn Leu Asp Phe Val Asn
            175                 180                 185

Leu Met Ala Tyr Asp Phe His Gly Ser Trp Glu Lys Val Thr Gly His
        190                 195                 200

Asn Ser Pro Leu Tyr Lys Arg Gln Glu Glu Ser Gly Ala Ala Ala Ser
    205                 210                 215

Leu Asn Val Asp Ala Ala Val Gln Gln Trp Leu Gln Lys Gly Thr Pro
220                 225                 230                 235

Ala Ser Lys Leu Ile Leu Gly Met Pro Thr Tyr Gly Arg Ser Phe Thr
                240                 245                 250

Leu Ala Ser Ser Ser Asp Thr Arg Val Gly Ala Pro Ala Thr Gly Ser
            255                 260                 265

Gly Thr Pro Gly Pro Phe Thr Lys Glu Gly Gly Met Leu Ala Tyr Tyr
        270                 275                 280

Glu Val Cys Ser Trp Lys Gly Ala Thr Lys Gln Arg Ile Gln Asp Gln
    285                 290                 295

Lys Val Pro Tyr Ile Phe Arg Asp Asn Gln Trp Val Gly Phe Asp Asp
300                 305                 310                 315

Val Glu Ser Phe Lys Thr Lys Val Ser Tyr Leu Lys Gln Lys Gly Leu
                320                 325                 330

Gly Gly Ala Met Val Trp Ala Leu Asp Leu Asp Asp Phe Ala Gly Phe
            335                 340                 345

Ser Cys Asn Gln Gly Arg Tyr Pro Leu Ile Gln Thr Leu Arg Gln Glu
        350                 355                 360

Leu Ser Leu Pro Tyr Leu Pro Ser Gly Thr Pro Glu Leu Glu Val Pro
    365                 370                 375

Lys Pro Gly Gln Pro Ser Glu Pro Glu His Gly Pro Ser Pro Gly Gln
380                 385                 390                 395

Asp Thr Phe Cys Gln Gly Lys Ala Asp Gly Leu Tyr Pro Asn Pro Arg
                400                 405                 410

Glu Arg Ser Ser Phe Tyr Ser Cys Ala Ala Gly Arg Leu Phe Gln Gln
            415                 420                 425

Ser Cys Pro Thr Gly Leu Val Phe Ser Asn Ser Cys Lys Cys Thr
        430                 435                 440

Trp Asn
    445
```

(2) INFORMATION FOR SEQ ID NO: 5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 5:

```
GACACTATAG AATAGGGC                                                 18
```

(2) INFORMATION FOR SEQ ID NO: 6:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:

```
TGGGATCATC AGCAGGACCA TGAAACCTGC CCAGGCCACA GACCGCACCA T            51
```

(2) INFORMATION FOR SEQ ID NO: 7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
TACATCTAGA ATTATGGCAA AACTGGTCTG CTACTTCACC                         40
```

(2) INFORMATION FOR SEQ ID NO: 8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
AGATCTAACC TTAGGTGCCT GAAGACAAGT ATGG                               34
```

(2) INFORMATION FOR SEQ ID NO: 9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
TACAGAATTC TTATTCACAT CCGGCCCTG                                     29
```

(2) INFORMATION FOR SEQ ID NO: 10:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
TACATCTAGA CTCCATCCAG AAAAACAGGT ATGG                        34
```

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

```
TCTAGAGTCG ACCTGCAGGC ATGCAAGCTT                             30
```

(2) INFORMATION FOR SEQ ID NO: 12:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

```
CGCAAGCTTG AGAGCTCCGT TCCGCCACAT GGTGCGGTCT GTGGCCTGGG       50
```

(2) INFORMATION FOR SEQ ID NO: 13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

```
GACTCTAGAC TAGGTGCCTG AAGGCAAGTA TG                          32
```

(2) INFORMATION FOR SEQ ID NO: 14:

(i) SEQUENCE CHARACTERISTICS:
        (A) LENGTH: 373 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Ala Lys Leu Val Cys Tyr Phe Thr Asn Trp Ala Gln Tyr Arg Gln Gly
 1               5                  10                  15

Glu Ala Arg Phe Leu Pro Lys Asp Leu Asp Pro Ser Leu Cys Thr His
                20                  25                  30
```

```
Leu Ile Tyr Ala Phe Ala Gly Met Thr Asn His Gln Leu Ser Thr Thr
        35                  40                  45

Glu Trp Asn Asp Glu Thr Leu Tyr Gln Glu Phe Asn Gly Leu Lys Lys
 50                  55                  60

Met Asn Pro Lys Leu Lys Thr Leu Leu Ala Ile Gly Gly Trp Asn Phe
 65                  70                  75                  80

Gly Thr Gln Lys Phe Thr Asp Met Val Ala Thr Ala Asn Asn Arg Gln
                 85                  90                  95

Thr Phe Val Asn Ser Ala Ile Arg Phe Leu Arg Lys Tyr Ser Phe Asp
             100                 105                 110

Gly Leu Asp Leu Asp Trp Glu Tyr Pro Gly Ser Gln Gly Ser Pro Ala
             115                 120                 125

Val Asp Lys Glu Arg Phe Thr Thr Leu Val Gln Asp Leu Ala Asn Ala
         130                 135                 140

Phe Gln Gln Glu Ala Gln Thr Ser Gly Lys Glu Arg Leu Leu Leu Ser
145                 150                 155                 160

Ala Ala Val Pro Ala Gly Gln Thr Tyr Val Asp Ala Gly Tyr Glu Val
                 165                 170                 175

Asp Lys Ile Ala Gln Asn Leu Asp Phe Val Asn Leu Met Ala Tyr Asp
             180                 185                 190

Phe His Gly Ser Trp Glu Lys Val Thr Gly His Asn Ser Pro Leu Tyr
         195                 200                 205

Lys Arg Gln Glu Glu Ser Gly Ala Ala Ala Ser Leu Asn Val Asp Ala
         210                 215                 220

Ala Val Gln Gln Trp Leu Gln Lys Gly Thr Pro Ala Ser Lys Leu Ile
225                 230                 235                 240

Leu Gly Met Pro Thr Tyr Gly Arg Ser Phe Thr Leu Ala Ser Ser Ser
                 245                 250                 255

Asp Thr Arg Val Gly Ala Pro Ala Thr Gly Ser Gly Thr Pro Gly Pro
             260                 265                 270

Phe Thr Lys Glu Gly Gly Met Leu Ala Tyr Tyr Glu Val Cys Ser Trp
         275                 280                 285

Lys Gly Ala Thr Lys Gln Arg Ile Gln Asp Gln Lys Val Pro Tyr Ile
         290                 295                 300

Phe Arg Asp Asn Gln Trp Val Gly Phe Asp Asp Val Glu Ser Phe Lys
305                 310                 315                 320

Thr Lys Val Ser Tyr Leu Lys Gln Lys Gly Leu Gly Gly Ala Met Val
                 325                 330                 335

Trp Ala Leu Asp Leu Asp Asp Phe Ala Gly Phe Ser Cys Asn Gln Gly
             340                 345                 350

Arg Tyr Pro Leu Ile Gln Thr Leu Arg Gln Glu Leu Ser Leu Pro Tyr
         355                 360                 365

Leu Pro Ser Gly Thr
         370

(2) INFORMATION FOR SEQ ID NO: 15:

(i) SEQUENCE CHARACTERISTICS:
        (A) LENGTH: 373 amino acids
        (B) TYPE: amino acid
        (C) STRANDEDNESS: single
        (D) TOPOLOGY: linear (ii) MOLECULE TYPE: peptide
```

-continued (xi) SEQUENCE DESCRIPTION: SEQ ID NO: 15:

Ala Lys Leu Val Cys Tyr Phe Thr Asn Trp Ala Gln Tyr Arg Gln Gly
1               5                   10                  15

Glu Ala Arg Phe Leu Pro Lys Asp Leu Asp Pro Ser Leu Cys Thr His
            20                  25                  30

Leu Ile Tyr Ala Phe Ala Gly Met Thr Asn His Gln Leu Ser Thr Thr
            35                  40                  45

Glu Trp Asn Asp Glu Thr Leu Tyr Gln Glu Phe Asn Gly Leu Lys Lys
50                  55                  60

Met Asn Pro Lys Leu Lys Thr Leu Leu Ala Ile Gly Gly Trp Asn Phe
65                  70                  75                  80

Gly Thr Gln Lys Phe Thr Asp Met Val Ala Thr Ala Asn Asn Arg Gln
            85                  90                  95

Thr Phe Val Asn Ser Ala Ile Arg Phe Leu Arg Lys Tyr Ser Phe Asp
            100                 105                 110

Gly Leu Asp Leu Asp Trp Glu Tyr Pro Gly Ser Gln Gly Ser Pro Ala
            115                 120                 125

Val Asp Lys Glu Arg Phe Thr Thr Leu Val Gln Asp Leu Ala Asn Ala
130                 135                 140

Phe Gln Gln Glu Ala Gln Thr Ser Gly Lys Glu Arg Leu Leu Leu Ser
145                 150                 155                 160

Ala Ala Val Pro Ala Gly Gln Thr Tyr Val Asp Ala Gly Tyr Glu Val
            165                 170                 175

Asp Lys Ile Ala Gln Asn Leu Asp Phe Val Asn Leu Met Ala Tyr Asp
            180                 185                 190

Phe His Gly Ser Trp Glu Lys Val Thr Gly His Asn Ser Pro Leu Tyr
            195                 200                 205

Lys Arg Gln Glu Glu Ser Gly Ala Ala Ala Ser Leu Asn Val Asp Ala
210                 215                 220

Ala Val Gln Gln Trp Leu Gln Lys Gly Thr Pro Ala Ser Lys Leu Ile
225                 230                 235                 240

Leu Gly Met Pro Thr Tyr Gly Arg Ser Phe Thr Leu Ala Ser Ser Ser
            245                 250                 255

Asp Thr Arg Val Gly Ala Pro Ala Thr Gly Ser Gly Thr Pro Gly Pro
            260                 265                 270

Phe Thr Lys Glu Gly Gly Met Leu Ala Tyr Tyr Glu Val Cys Ser Trp
            275                 280                 285

Lys Gly Ala Thr Lys Gln Arg Ile Gln Asp Gln Lys Val Pro Tyr Ile
            290                 295                 300

Phe Arg Asp Asn Gln Trp Val Gly Phe Asp Asp Val Glu Ser Phe Lys
305                 310                 315                 320

Thr Lys Val Ser Tyr Leu Lys Gln Lys Gly Leu Gly Gly Ala Met Val
            325                 330                 335

Trp Ala Leu Asp Leu Asp Asp Phe Ala Gly Phe Ser Cys Asn Gln Gly
            340                 345                 350

Arg Tyr Pro Leu Ile Gln Thr Leu Arg Gln Glu Leu Ser Leu Pro Tyr
            355                 360                 365

Leu Ser Ser Gly Thr
370

-continued (2) INFORMATION FOR SEQ ID NO: 16:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer"

(xi) SEQUENCE DESCRIPTION: SEQ ID NO: 16:

```
TGATACGGTA CCGCCCCATG GCTGACTA                                28
```

(2) INFORMATION FOR SEQ ID NO: 17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 17:

```
GCAAGTTTGG CGCGAAATCG                                         20
```

CHITINASE MATERIALS AND METHODS

This is a continuation-in-part of U.S. application Ser. No. 08/663,618 filed Jun. 14, 1996.

FIELD OF THE INVENTION

The present invention relates generally to human chitinase enzyme and more specifically to novel purified and isolated polynucleotides encoding human chitinase, to the chitinase products encoded by the polynucleotides, to materials and methods for the recombinant production of chitinase products and to antibody substances specific for the chitinase.

BACKGROUND

Chitin is a linear homopolymer of β-(1,4)-linked N-acetylglucosamine residues. This polysaccharide is second only to cellulose as the most abundant organic substance. The exoskeleton of arthropods is composed of chitin. In addition, fungi and other parasites contain chitin in their outer cell wall, where it serves important structural and protective roles. Disruption of the fungal cell wall and membrane has been a useful therapeutic strategy against fungi and parasites. For example, Amphotericin B and fluconazole exert their anti-fungal activity by affecting membrane steroids. Despite the existence of anti-fungal therapeutics, fungal infections of humans have increasingly become responsible for life-threatening disorders. See, Georgopapadakou et al., *Trends Microbiol.*, 3: 98–104 (1995). The fungal species and parasites responsible for these diseases are mainly Canrda, Aspergillus, Cryptococcus, Histoplasma, Coccidioides and Pneumocystis. These pathogens are particularly dangerous in immuno-compromised individuals, such as patients with AIDS, patients undergoing chemotherapy, and immunosuppressed organ transplant patients.

Chitin can be degraded by the enzyme chitinase. Chitinase enzymes are found in plants, microorganisms, and animals. Bacterial chitinase helps to provide a carbon source for bacterial growth. Insects produce chitinase to digest their cuticle at each molt. In plants, chitinase is thought to provide a protective role against parasitic fungi. Chitinases have been cloned from numerous bacterial [e.g., *Serratia marcescens*, Jones et al., *EMBO J.*, 5:467–473 (1986)], plant [e.g., tobacco, Heitz et al., *Mol. Gen. Genet.*, 245:246–254 (1994)], and insect [e.g., wasp, Krishnan et al., *J. Biol. Chem.*, 269:20971–20976 (1994)] species.

Several proteins with low homology to bacterial, insect, and plant chitinases (less than 40% amino acid identity) have been identified in mammals, such as human cartilage gp-39 (C-gp39) [Hakala et al., *J. Biol. Chem.*, 268.25803–25810 (1993)], human glycoprotein YKL-40 [Johansen et al., *Eur. J. Cancer*, 31A: 1437–1442 (1995)], oviduct-specific, estrogen-induced protein from sheep [DeSouza et al., *Endocrinology*, 136:2485–2496 (1995)], cows and humans; and a secretory protein from activated mouse macrophages [Chang et al., Genbank M94584]. However, chitin-degrading activity has not been reported for these proteins. The function of these proteins is not known, but they have been postulated to be involved in tissue remodeling. Hakala et al., supra, report that C-gp39 is detectable in synovial and cartilage specimens from rheumatoid arthritis patients, but not from normal humans. Recklies et al., *Athritis Rheumatism*, 36(9 SUPPL.):S190 (1993) report localization of the C-gp39 protein to a distinct population of cells in the superficial layers of cartilage. Johansen et al., supra, report that measurements of YKL-40 serum levels are of value as a potential prognostic marker for the extent of metastatic disease and survival of patients with recurrent breast cancer.

Escott et al., *Infect. Immun.*, 63:4770–4773 (1995) demonstrated chitinase enzymatic activity in human leukocytes and in human serum. Overdijk et al., *Glycobiology*, 4:797–803 (1994) described isolation of a chitinase (4-methylumbelliferyl-tetra-N-acetylchitotetraoside hydrolase) from human serum and rat liver. Renkema et al., *J. Biol. Chem.*, 270:2198–2202 (February 1995) prepared a human chitotriosidase from the spleen of a Gaucher disease patient. Their preparation exhibited chitinase activity and the article reports a small amount of amino acid sequence of the protein component of the preparation (22 amino terminal residues and 21 residues of a tryptic fragment). The function of human chitinase is also unknown, but a relationship with the pathophysiology of Gaucher disease is proposed in the article. A later publication by the same group [Boot et al., *J. Biol. Chem.*, 270(44):26252–26256 (November 1995)] describes the cloning of a human macrophage cDNA encoding a product that exhibits chitinase activity. The partial amino acid sequence reported by the group in their February 1995 article matches portions of the deduced amino acid sequence of the human macrophage cDNA product. See also International Patent Publication No. WO 96/40940.

In view of the increasing incidence of life-threatening fungal infection in immunocompromised individuals, there exists a need in the art to identify and isolate polynucleotide sequences encoding human chitinases, to develop materials and methods useful for the recombinant production of the enzyme, and to generate reagents for the detection of the chitinase in plasma.

SUMMARY OF THE INVENTION

The present invention provides novel purified and isolated polynucleotides (i.e., DNA and RNA, both sense and antisense strands) encoding human chitinase or fragments and analogs thereof; methods for the recombinant production of chitinase polypeptides, fragments and analogs thereof; purified and isolated chitinase polypeptide fragments and analogs; antibodies to such polypeptides, fragments and analogs; and pharmaceutical compositions comprising these polypeptides, fragments, analogs, or antibodies.

Specifically provided are: purified, isolated polynucleotides encoding the human chitinase amino acid sequence of SEQ ID NOS: 2 or 4, particularly amino acids 1 to 445 thereof; DNAs comprising the protein coding nucleotides of SEQ ID NOS: 1 or 3, particularly nucleotides 65 to 1402 of SEQ ID NO: 1 or nucleotides 90 to 1427 of SEQ ID NO: 3; purified, isolated polynucleotides comprising a polynucleotide sequence encoding the amino acid sequence of SEQ ID NOS: 14 or 15; purified, isolated polynucleotides encoding human chitinase selected from the group consisting of: (a) a double-stranded DNA comprising the protein coding portions of the sequence set out in either SEQ ID NO: 1 or SEQ ID NO: 3, (b) a DNA which hybridizes under stringent conditions to a non-coding strand of the DNA of (a), and (c) a DNA which, but for the redundancy of the genetic code, would hybridize under stringent conditions to a non-coding strand of DNA sequence of (a) or (b); vectors comprising such DNAs, particularly expression vectors wherein the DNA is operatively linked to an expression control DNA sequence; host cells stably transformed or transfected with such DNAs in a manner allowing the expression in said host cell of human chitinase; a method for producing human chitinase comprising culturing such host cells in a nutrient medium and isolating human chitinase from said host cell or said nutrient medium; purified, isolated polypeptides produced by this method; purified, isolated polypeptides comprising the human chitinase amino acid sequence of SEQ ID NOS: 2 or 4, particularly amino acids 1 to 445 thereof; human chitinase fragments lacking from 1 to about 72 C-terminal amino acid residues of mature human chitinase, particularly the human chitinase fragment of SEQ ID NO: 14; the human chitinase analog of SEQ ID NO: 15; hybridoma cell lines producing a monoclonal antibody that is specifically reactive with one of the above-described polypeptides; and monoclonal antibodies produced by such hybridomas.

Preferred DNA sequences of the invention include genomic and cDNA sequences as well as wholly or partially chemically synthesized DNA sequences. The nucleotide sequence of two human cDNAs encoding presumed allelic variants of human chitinase, and including noncoding 5' and 3' sequences, are set forth in SEQ ID NO: 1 and SEQ ID NO: 3. These DNA sequences and DNA sequences which hybridize to the noncoding strand thereof under standard stringent conditions or which would hybridize but for the redundancy of the genetic code, are contemplated by the invention. Preferred DNAs of the present invention comprise the human chitinase coding region (corresponding to nucleotides 2 to 1402 of SEQ ID NO: 1 or nucleotides 27 to 1427 of SEQ ID NO: 3), and the putative coding sequence of the mature, secreted human chitinase protein without its signal sequence (nucleotides 65 to 1402 of SEQ ID NO: 1, or nucleotides 90 to 1427 of SEQ ID NO: 3).

Exemplary stringent hybridization conditions are as follows: hybridization at 42° C. in 50% formamide and washing at 60° C. in 0.1×SSC, 0.1% SDS. It is understood by those of skill in the art that variation in these conditions occurs based on the length and GC nucleotide base content of the sequences to be hybridized. Formulas standard in the art are appropriate for determining exact hybridization conditions. See Sambrook et al., 9.47–9.51 in Molecular Cloning, Cold Spring Harbor Laboratory Press, Cold Spring Harbor, N.Y. (1989).

Two amino acid sequences for human chitinase(s) are set forth in SEQ ID NOS: 2 and 4. The sequence of SEQ ID NO: 2 is encoded by the nucleotide sequence of SEQ ID NO: 1, and SEQ ID NO: 4 is encoded by the nucleotide sequence of SEQ ID NO: 3. Preferred polynucleotides of the present invention include, in addition to those polynucleotides described above, polynucleotides that encode amino acids −21 to 445 of SEQ ID NO: 2 or SEQ ID NO: 4, and that differ from the polynucleotides described in the preceding paragraphs only due to the well-known degeneracy of the genetic code. Similarly, since twenty-one amino acids (positions −21 to −1) of SEQ ID NOS: 2 and 4 comprise a signal peptide that is cleaved to yield the mature human chitinase protein, preferred polynucleotides include those encoding polypeptides comprising amino acids 1 to 445 of SEQ ID NO: 2 or SEQ ID NO: 4.

Among the uses for the polynucleotides of the present invention is use as a hybridization probe, to identify and isolate genomic DNA encoding human chitinase; to identify and isolate non-human genes encoding proteins homologous to human chitinase; to identify human and non-human proteins having similarity to human chitinase (including those that may be involved in tissue remodeling); and to identify those cells which express human chitinase and the biological conditions under which this protein is expressed.

In another aspect, the invention includes biological replicas (i.e., copies of isolated DNA sequences made in vivo or in vitro) of DNA sequences of the invention. Autonomously replicating recombinant constructions such as plasmid and viral DNA vectors incorporating chitinase polynucleotides, including any of the DNAs described above, are provided. Preferred vectors include expression vectors in which the incorporated chitinase-encoding cDNA is operatively linked to an endogenous or heterologous expression control sequence and a transcription terminator. Such expression vectors may further include polypeptide-encoding DNA sequences operably linked to the chitinase-encoding DNA sequences, which vectors may be expressed to yield a fusion protein comprising the polypeptide of interest.

According to another aspect of the invention, procaryotic or eucaryotic host cells are stably transformed or transfected with DNA sequences of the invention in a manner allowing the desired chitinase product to be expressed therein. Host cells expressing chitinase products can serve a variety of useful purposes. Such cells constitute a valuable source of immunogen for the development of antibody substances specifically immunoreactive with chitinase. Host cells of the invention are useful in methods for the large scale production of chitinase wherein the cells are grown in a suitable culture medium and the desired polypeptide products are isolated, e.g., by immunoaffinity purification, from the cells or from the medium in which the cells are grown.

Chitinase products may be obtained as isolates from natural cell sources or may be chemically synthesized, but are preferably produced by recombinant procedures involving procaryotic or eucaryotic host cells of the invention. Chitinase products of the invention may be full length polypeptides, fragments or analogs thereof. Chitinase products having part or all of the amino acid sequence set out in SEQ ID NO: 2 or SEQ ID NO: 4 are contemplated. One preferred fragment which lacks the C-terminal seventy-two amino acid residues of the mature protein is set forth in SEQ ID NO: 14. It has been determined that these seventy-two C-terminal residues are not critical to chitinase enzymatic activity. Example 5 illustrates production of this C-terminal fragment; the introduction of a stop codon after the codon for amino acid 373 resulted in a recombinant chitinase fragment of about 39 kDa that retained similar specific activity when compared with full length recombinant human chitinase.

Analogs may comprise chitinase analogs wherein one or more of the specified (i.e., naturally encoded) amino acids is deleted or replaced or wherein one or more nonspecified amino acids are added: (1) without loss of one or more of the enzymatic activities or immunological characteristics specific to chitinase; or (2) with specific disablement of a particular biological activity of chitinase. Example 3 illustrates the production of such an analog (SEQ ID NO: 15), in which the proline at position 370 is substituted with a serine, and in which the C-terminal seventy-two amino acid residues have been deleted. The use of mammalian host cells is also expected to provide for post-translational modifications (e.g., myristolation, glycosylation, truncation, lipidation and tyrosine, serine or threonine phosphorylation) as may be needed to confer optimal biological activity on recombinant expression products of the invention.

Proteins or other molecules that bind to chitinase may be used to modulate its activity. Also comprehended by the present invention are antibody substances (e.g., monoclonal and polyclonal antibodies, single chain antibodies, chimeric antibodies, CDR-grafted antibodies and the like) and other binding proteins specific for chitinase. Proteins or other molecules (e.g., small molecules) which specifically bind to chitinase can be identified using chitinase isolated from plasma, recombinant chitinase, chitinase variants or cells expressing such products. Binding proteins are useful, in turn, in compositions for immunization as well as for purifying c.hitinase, and are useful for detection or quantification of chitinase in fluid and tissue samples by known immunological procedures. Anti-idiotypic antibodies specific for chitinase-specific antibody substances are also contemplated.

The scientific value of the information contributed through the disclosures of DNA and amino acid sequences of the present invention is manifest. As one series of examples, knowledge of the sequence of a cDNA for chitinase makes possible the isolation by DNA/DNA hybridization of genomic DNA sequences encoding chitinase and chitinase expression control regulatory sequences such as promoters, operators and the like. DNA/DNA hybridization procedures carried out with DNA sequences of the invention under conditions of stringency standard in the art are likewise expected to allow the isolation of DNAs encoding human allelic variants of chitinase, other structurally related human proteins sharing one or more of the biochemical and/or immunological properties of chitinase, and non-human species proteins homologous to chitinase. The DNA sequence information provided by the present invention also makes possible the development, by homologous recombination or "knockout" strategies [see, e.g., Kapecchi, *Science*, 244: 1288–1292 (1989)], of rodents that fail to express a functional chitinase enzyme, overexpress chitinase enzyme, or express a variant chitinase enzyme. Polynucleotides of the invention when suitably labelled are useful in hybridization assays to detect the capacity of cells to synthesize chitinase. Polynucleotides of the invention may also be the basis for diagnostic methods useful for identifying a genetic alteration(s) in the chitinase locus that underlies a disease state or states. Also made available by the invention are anti-sense polynucleotides relevant to regulating expression of chitinase by those cells which ordinarily express the same.

Administration of chitinase preparations of the invention to mammalian subjects, especially humans, for the purpose of ameliorating disease states caused by chitin-containing parasites such as fungi is contemplated by the invention. Fungal infections (mycoses) such as candidiasis, aspergillosis, coccidioidomycosis, blastomycosis, paracoccidioidomycosis, histoplasmosis, cryptococcosis, chromoblastomycosis, sporotrichosis, mucormycosis, and the dermatophytoses can manifest as acute or chronic disease. Pathogenic fungi cause serious, often fatal disease in immunocompromised hosts. Cancer patients undergoing chemotherapy, immunosuppressed individuals, and HIV-infected individuals are susceptible to mycoses caused by Candida, Aspergillus, *Pneumocystis carinii*, and other fungi. Amphotericin B and fluconazole are useful therapeutics for fungal infections, but toxicity associated with these drugs causes serious adverse side effects that limit their usefulness. The mortality of systemic candidiasis is greater than 50% despite Amphotericin B treatment. Therefore, a need exists for agents that inhibit fungal growth in vivo; and such products may be used as single agents or in combination with currently approved, conventional anti-fungal compounds. Because growing fungi require chitin synthesis for survival, inhibition by recombinant human chitinase may be useful for limiting fungal infections in vivo. Animal models for fungal infection are illustrated below in Examples 8 through 14 and have been described in the art.

Specifically contemplated by the invention are chitinase compositions for use in methods for treating a mammal susceptible to or suffering from fungal infections comprising administering chitinase to the mammal in an amount sufficient to supplement endogenous chitinase activity. It is contemplated that the chitinase may be administered with other conventional anti-fungal agents, including amphotericin B and the structurally related compounds nystatin and pimaricin; 5-fluorocytosine; azole derivatives such as fluconazole, ketoconazole, clotrimazole, miconazole, econazole, butoconazole, oxiconazole, sulconazole, terconazole, itraconazole and tioconazole; allylamines-thiocarbamates, such as tolnaftate, naftifine and terbinafme; griseofulvin; ciclopirox olamine; haloprogin; undecylenic acid; and benzoic acid. [See, e.g., Goodman & Gilman, The Pharmacological Basis of Therapeutics, 9th ed., McGraw-Hill, NY (1996).] Chitinase may improve the effectiveness of these conventional anti-fungal agents, perhaps by rendering the yeast more susceptible to their action, even in situations where the chitinase alone is not effective for inhibiting growth of fungi. By reducing the amount of conventional anti-fungal agent needed to exert the desired therapeutic effect, chitinase may allow the drugs to be used at less toxic levels. For example, Davies and Pope, *Nature*, 273:235–236 (1978) reported that administration of mycolases (enzymes that degrade the fungal cell wall) in conjunction with a normally ineffective dose of anti-fungal drug to Aspergillus-infected mice provided synergistically effective treatment. The combination of fungal chitinase and laminarinase was noted to be more effective in attacking the fungal cell wall than either enzyme alone.

Thus, the invention contemplates the use of chitinase in the preparation of a medicament for the prophylactic or therapeutic treatment of fungal infections, and further contemplates the use of chitinase in the preparation of a medicament for co-administration with another anti-fungal agent.

Therapeutic/pharmaceutical compositions contemplated by the invention include chitinase and a physiologically acceptable diluent or carrier and may also include other anti-fungal agents. Dosage amounts indicated would be sufficient to supplement endogenous chitinase activity. For general dosage considerations see *Remington: The Science and Practice of Pharmacy*, 19th ed., Mack Publishing Co., Easton, Pa. (1995). Dosages will vary between about 1 gg/kg to 100 mg/kg body weight, and preferably between about 0.1 to about 20 mg chitinase/kg body weight. Therapeutic compositions of the invention may be administered by various routes depending on the infection to be treated, including via subcutaneous, intramuscular, intravenous, intrapulmonary, transdermal, intrathecal, topical, oral, or suppository administration.

The invention also contemplates that the overexpression of chitinase in Gaucher disease or at sites of inflammation (such as in rheumatoid arthritis) may have deleterious effects on the extracellular matrix and, in such disease settings, inhibitors of chitinase activity may provide therapeutic benefit, e.g. by reducing remodeling or destruction of the extracellular matrix.

The human chitinase cDNA of the present invention was isolated from a macrophage cDNA library. Macrophages are known to be closely associated with rheumatoid arthritis lesions [Feldman et al., *Cell*, 85:307–310 (1996)], and macrophage products such as TNF-α are implicated in disease progression. A protein with homology to human chitinase, C-gp39, has been detected in the synovium and cartilage of rheumatoid arthritis patients. While the natural substrate for human chitinase is probably chitin from pathogenic organisms, the enzyme may also exhibit activity on endogenous macromolecules which form the natural extracellular matrix. For example, it has been suggested that hyaluronic acid, a major component of the extracellular matrix, contains a core of chitin oligomers. [Semino et al., *Proc. Nat'l Acad. Sci.*, 93:4548–4553 (1996); Varki, *Proc. Nat'l. Acad. Sci.*, 93:4523–4525 (1996).] Chitinase may therefore be involved in degradation of extracellular matrix in diseases such as rheumatoid arthritis. The role of chitinase may be determined by measuring chitinase levels and/or the effects of chitinase administration or chitinase inhibition in synovial fluid isolated from arthritic joints. Endogenous chitinase levels can be measured by enzymatic assay or with an antibody. Viscosity of synovial fluid can be measured before and after chitinase treatment; a decrease of viscosity associated with chitinase would be consistent with an endogenous chitinase substrate. Modulation of chitinase activity could thereby modulate the progression of joint destruction in rheumatoid arthritis.

Also contemplated by the invention are methods for screening for inhibitors of chitinase activity, which may be useful in the manner described in the preceding paragraph. A method for screening samples to identify agents that inhibit chitinase is reported in, e.g., WO 95/34678 published Dec. 21, 1995.

Further contemplated are methods for measuring endogenous levels of chitinase, e.g., for diagnosing Gaucher's disease. Hollak et al., *J. Clin. Invest.*, 93:1288–1292 (1994), report that plasma chitinase levels are a diagnostic marker for Gaucher's disease. The recombinant proteins of this invention are expected to be more useful than preparations purified from humans, which have associated problems of yield and contamination with other impurities or infectious agents.

DETAILED DESCRIPTION

Other aspects and advantages of the present invention will be understood upon consideration of the following illustrative examples. Example 1 describes the isolation of human chitinase cDNA clones from a human macrophage cDNA library. Example 2 addresses the pattern of chitinase gene expression in various human tissues. Example 3 describes the recombinant expression of the human chitinase gene in prokaryotic cells and purification of the resulting enzyme. Example 4 provides a protocol for the recombinant production of human chitinase in yeast. Example 5 describes the recombinant expression of the human chitinase gene in mammalian cells and purification of the resulting protein. Example 6 describes production of human chitinase polypeptide analogs by peptide synthesis or recombinant production methods. Example 7 provides a protocol for generating monoclonal antibodies that are specifically immunoreactive with human chitinase. Example 8 describes an assay for the measurement of chitinase catalytic activity. Example 9 addresses determination of the anti-fungal activity of human chitinase in vitro. Example 10 addresses determination of the anti-fungal activity of human chitinase in vivo in a mouse model, and Examples 11 through 14 address rabbit models of invasive aspergillosis, disseminated candidiasis, Candida ophthalmitis, and Candida endocarditis.

EXAMPLE 1

Isolation of Chitinase cDNA Clones

A cDNA library was prepared from peripheral blood monocyte-derived macrophages as described in Tjoelker et al., *Nature*, 374:549–552 (1995). Clones from the library were randomly chosen and plasmid DNA was purified from individual clones. The sequence of approximately 300 to 500 bases from the end of DNA from each clone was determined on an automated sequencer (Model 373, Applied Biosystems, Foster City, Calif.) using primer JHSP6, which hybridizes to the plasmid vector pRc/CMV (Invitrogen, San Diego, Calif.) adjacent to the cDNA cloning site:

JHSP6: 5'-GACACTATAGAATAGGGC-3' (SEQ ID NO: 5)

The nucleotide and deduced amino acid sequence of these cDNA clones were compared to sequences in nucleotide and peptide sequence databases to determine similarity to known genes. Sequence comparisons were performed by the BLAST Network Service of the National Center for Biotechnology Information using the alignment algorithm of Altschul et al., *J. Mol. Biol.*, 215:403–410 (1990). Clone MO-911 exhibited significant homology to several different sequences, including mouse macrophage secretory protein YM-1 precursor (Genbank accession no. M94584), human cartilage gp-39 (Hakala et al., supra), oviductal glycoprotein from sheep, cow, and humans (DeSouza et al., supra), and chitinases from parasite (Oncocerca, Genbank accession no. U14639), wasp (Chelonus, Genbank accession no. U10422), plant (Nicotiana, Genbank accession no. X771 11), and bacteria (Serratia, Genbank accession no. Z36295); its highest observed homology was to mammalian genes that encoded proteins with chitinase homology but no demonstrated chitinase activity. Further sequence analysis of MO-911 suggested that it contained a portion of the coding region for a human chitinase homolog.

The DNA sequence of clone pMO-218 (deposited on Jun. 7, 1996 under the terms of the Budapest Treaty with the American Type Culture Collection, 12301 Parklawn Drive, Rockville, Md. 20852, U.S.A. under Accession No. 98077) is set forth in SEQ ID NO: 1, and the encoded amino acid sequence is set forth in SEQ ID NO: 2. MO-218 appeared to include the entire coding region of the human chitinase cDNA (nucleotides 2 to 1402 of SEQ ID NO: 1), which comprises a twenty-one amino acid putative signal sequence followed by 445 encoded amino acids (residues 1 to 445 of SEQ ID NO: 2). The twenty-two amino acids following the putative signal sequence exactly match the aminoterminal sequence of purified human chitotriosidase reported in Renkema et al., supra.: Renkema et al. also described a twenty-one amino acid sequence from a tryptic fragment of human chitotriosidase which corresponds exactly to residues 157 to 177 of MO-218 (SEQ ID NO: 2). Boot et al., supra, report the cloning of a human chitotriosidase cDNA which contains a coding sequence essentially identical to that of MO-218. The sequence of MO-218 differs from Boot et al. by an additional fourteen nucleotides at the 5' end and by a nucleotide change at nucleotide 330 in the coding region.

To confirm that MO-218 indeed contained the entire coding region of the cDNA, a $^{32}$P-labelled probe P-1 (TGGGATCATCAGCAGGACCATGAAACCTGCCCAG-GCCACAGACCGCACCAT, SEQ ID NO: 6) was prepared that corresponded to the complement of nucleotides 2 through 52 of MO-218 (SEQ ID NO: 1). Probe P-1 was designed to hybridize with clones that are at least as long as MO-218 at the 5' end. The probe was hybridized with a portion (approximately 30,000 clones) of the human macrophage cDNA library described above, in 40% formamide and hybridization buffer (5×SSPE, 10×Denhardt's, 100 μg/ml denatured salmon sperm DNA, and 2% SDS) at 42° C. overnight. The filters were washed and three clones that hybridized were chosen for sequence/analysis. The longest clone was designated pMO-13B (deposited on Jun. 7, 1996 under the terms of the Budapest Treaty with the American Type Culture Collection, 12301 Parklawn Drive, Rockville, Md. 20852, U.S.A. under Accession No. 98078). The DNA sequence of pMO-13B is set forth in SEQ ID NO: 3 and the encoded amino acid sequence is set forth in SEQ ID NO: 4. This clone contains 25 additional nucleotides at the 5' end compared-with MO-218; in addition, MO-13B (SEQ ID NO: 3) contains one nucleotide substitution at nucleotide 330 (corresponding to nucleotide 305 of MO-218, SEQ. ID NO: 1) which changes the encoded amino acid at position 80 of the mature protein from a glycine (in SEQ ID NO: 2) to a serine (in SEQ ID NO: 4).

EXAMPLE 2

Chitinase Gene Expression Pattern in Human Tissues

Northern blot analysis was performed to identify tissues in which the human chitinase is expressed. A multiple human tissue Northern blot (Clontech, Palo Alto Calif.) was hybridized with the entire coding region of MO-218 under standard stringent conditions (according to the Clontech laboratory manual). Greatest hybridization was observed to lung tissue (+++) and ovary (+++), with much smaller levels (+) in thymus and placenta. The size of the hybridizing mRNA was 2.0 kb for lung, ovary and thymus, which corresponds well with the size of the cloned cDNA (1.6 kb, or about 1.8 kb including the polyA tail). The size of the hybridizing placental mRNA was considerably smaller, at 1.3 kb. Chitinase hybridization was not observed in spleen, prostate, testes, small intestine, colon, peripheral blood leukocytes, heart, brain, liver, skeletal muscle, kidney, or pancreas. Chitinase expression in lung is consistent with a protective role against pathogenic organisms that contain chitin, since the lung represents the primary route of entry for fungal pathogens.

EXAMPLE 3

Production of Recombinant Human Chitinase in Bacterial Cells

The mature coding region of MO-218 was engineered for expression in *E. coli* as a C-terminal truncated analog. PCR was used to generate a DNA fragment for expression using a primer corresponding to nucleotides 65 to 88 of the MO-218 chitinase cDNA preceded by an initiating methionine codon and an XbaI restriction endonuclease site (5'-TACATCTAGAATTATGGCAAAACTGGTCTGCT-ACTTCACC-3', SEQ ID NO: 7), and a downstream primer encoding nucleotides 1163 to 1183 of MO-218 followed by a stop codon and a HindIII site (5'-AGATCTAACCTTA-GGTGCCTGAAGACAAGTATGG-3', SEQ ID NO: 8). The downstream primer contained an adenine at base 25, while the MO-218 sequence contains a guanine at the corresponding nucleotide position. Consequently, the resulting DNA fragment contains a thymine rather than a cytosine at the position corresponding to nucleotide 1172 of the MO-218 sequence, and the encoded chitinase fragment, set forth in SEQ ID NO: 15, is also an analog that contains a serine at mature amino acid position 370 instead of the proline encoded by-MO-218. The resulting DNA fragment was digested with XbaI and HindIII and cloned into plasmid pAraBAD (which is also known by the designation pAraCB).

Plasmid pAraCB was prepared as follows. Plasmid pUC19 was modified to include an arabinose promoter and subsequently to include AKAP 79 encoding sequences. The arabinose promoter [Wilcox et al., *Gene*, 34:123–128 (1985); Wilcox, et al., *Gene*, 18:157–163 (1982)] and the araC gene were amplified by PCR from the arabinose operon BAD of Salmonella typhimurium as an EcoRI/XbaI fragment with the primers araC-2 (SEQ ID NO: 9) and arab-1 (SEQ ID NO: 10):

```
                                      SEQ ID NO: 9
araC-2   TACAGAATTCTTATTCACATCCGGCCCTG SEQ ID NO: 10
arab-1   TACATCTAGACTCCATCCAGAAAAACAGGTATGG
```

Primer araC-2 encodes an EcoRI site (underlined) and a termination codon (italics) for the araC gene product. Primer arab-1 encodes a putative ribosome binding domain (italics) and an XbaI restriction site (underlined). PCR with these primers produced a 1.2 kb fragment which was digested with EcoRI and XbaI and subcloned into pUC19 (New England Biolabs, Beverly, Mass.) previously digested with the same two enzymes. The resulting plasmid was designated araCB and contained a polylinker region (SEQ ID NO: 11) flanked at the 5' end with a XbaI restriction site (underlined) and at the 3' end with a HindIII site (italics).

```
                                      SEQ ID NO: 11
araCB polylinker   TCTAGAGTCGACCTGCAGGCATGCAAGCTT
```

Transformants containing the resulting expression plasmid (pAraMO218) were induced with arabinose and grown at 37° C. These transformants produced inclusion bodies containing a 39 kDa protein which was a truncated form of chitinase (engineered to contain 373 instead of 445 amino acids). This chitinase fragment contains four cysteine residues, while the full length chitinase contains ten cysteine residues. The inclusion bodies were separated from the *E. coli* culture and electrophoresed on SDS-PAGE. The 39 kDa band was transferred to a PVDF membrane and amino terminal sequenced. The majority (about two-thirds) of the material contained a sequence corresponding to the amino terminus of human chitinase. The remaining material corresponded to a contaminating *E. coli* protein, porin. This recombinant chitinase preparation from *E. coli* was useful for producing polyclonal and monoclonal antibodies (described below in Example 7).

When transformants containing the Ara-chitinase expression plasmid were grown at 25° C., inclusion bodies were not observed and expression of recombinant product was decreased from about ten percent of total cell protein to about one percent. However, this material produced at 25° C. exhibited chitinase catalytic activity.

EXAMPLE 4

Production of Recombinant Human Chitinase in Yeast Cells

Exemplary protocols for the recombinant expression of human chitinase in yeast and for the purification of the resulting recombinant protein follow. The coding region of human chitinase is engineered into vectors for expression in *Saccharomyces cerevisiae* using either PCR or linker oligonucleotides designed to encode a fusion polypeptide containing a secretion mediating leader to the coding region for human chitinase corresponding to the amino terminus of the natural molecule. Secretion signal peptides include, e.g., SUC2 or equivalent leaders with a functional signal peptidase cleavage site, or pre-pro-alpha factor or other complex leader composed of a pre, or signal peptide, and a pro, or spacer region, exhibiting a KEX2 cleavage site. The DNA encoding the signal sequence can be obtained by oligonucleotide synthesis or by PCR. The DNA encoding the pre-pro-alpha factor leader is obtained by PCR using primers containing nucleotides 1 through 20 of the alpha mating factor gene and a primer complementary to nucleotides 255 through 235 of this gene [Kujan and Herskowitz, *Cell*, 30.933–943 (1982)). The pre-pro-alpha leader coding sequence and human chitinase coding sequence fragments are ligated into a plasmid containing the yeast alcohol dehydrogenase (ADH2) promoter, such that the promoter directs the expression of a fusion protein. As taught by Rose and Broach, [Meth. Enz., 185:234–279, D. Goeddel, ed., Academic Press, Inc., San Diego, Calif. (1990)], the vector further includes an ADH2 transcription terminator downstream of the cloning site, the yeast "2-micron" replication origin, a selectable marker, for example TRP1, CUP1 or LEU2 (or LEU2-d) or other equivalent gene, the yeast REP1 and REP2 genes, the *E. coli* beta lactamase gene, and an *E. coli* origin of replication. The beta-lactamase and TRP1 genes provide for selection in bacteria and yeast, respectively. The REP1 and REP2 genes encode proteins involved in plasmid copy number replication.

Alternatively, other fusion points within the chitinase coding region may be chosen. Truncates of the coding region may be used to increase homogeneity of the product, increase the specific activity or alter the substrate specificity.

The DNA constructs described in the preceding paragraphs are transformed into yeast cells using a known method, e.g. lithium acetate treatment [Stearns et al., *Meth. Enz.*, supra, pp. 280–297] or by equivalent methods. The ADH2 promoter is induced upon exhaustion of glucose in the growth media [Price et al., *Gene*, 55:287 (1987)]. The pre-pro-alpha sequence or other leader sequence effects secretion of the fusion protein, releasing the mature human chitinase peptide from the cells. The signal peptide leader is processed by signal peptidase or, in the case of pre-pro-alpha removal of the pro region, by the KEX2 protease Bfitter et al., *Proc. Natl. Acad. Sci. USA*, 81:5330–5334 (1984)].

Chitinase contains in its mature amino acid sequence two dibasic sequences at positions 107–108 (Lys-Arg) and 209–210 (Arg-Lys) that may be proteolytically clipped by the KEX2 protease during secretion. To stabilize and/or increase the level of product secreted from cells, these sequences could be mutated to eliminate the potential sites for proteolysis as shown by Gillis et al. [*Behring Inst. Mitt.*, No. 83:1–7 (1988)] or by expressing chitinase without dibasic modifications in a host that is deficient in KEX2. Such hosts can be obtained either by screening for non-KEX2 protease containing mutants, or by manipulation of the genomic KEX2 locus by gene replacement/gene disruption techniques [Orr-Weaver et al., *Proc. Natl. Acad. Sci, USA*, 78:6354–6358 (1981)].

Recombinant chitinase may be secreted from *Saccharomyces cerevisiae* using similar vectors containing alternative promoters PRB1, GALA, TPI, or other suitably strong promoters bearing fragments or by fusion to a variety of leader sequences [Sleep et al., *Bio/Technol.*, 8:4246 (1990)].

Other non-*Saccharomyces cerevisiae* suitable expression hosts include *Kluyveromyces lactis, Schizosaccharomyces pombe, Pichia pastoris* and members of the Hansenula or Aspergillus geni. Analogous recombinant expression systems for these fungi include the organism and their appropriate autonomously replicating vector [e.g. Falcone et al., *Plasmnd*, 15:248–252 (1988)] or multiply integrated expression cassettes. These systems also rely on signal sequences or leaders of the types described above to mediate secretion into the medium.

The secreted recombinant human chitinase is purified from the yeast growth medium by, e.g., the methods used to purify chitinase from bacterial and mammalian cell supernatants (see Example 3 above and Example 5 below).

Alternatively, the mature form of the recombinant chitinase product may be expressed in the cytoplasms of the *Saccharomyces cerevsiae* cells or analogous host, and purified from the lysed host cells. The protein may be refolded during the act of purification to obtain appropriate levels of specific activity.

EXAMPLE 5

Production of Recombinant Human Chitinase in Mammalian cells

A. Expression in COS cells

The MO-218 clone and the MO-13B clone, both of which contain full length human chitinase cDNA 3' to the CMV promoter of pRc/CMV, were isolated. A third plasmid, which corresponded to the same C-terminal fragment expressed in bacterial cells in Example 3 above, was prepared as follows. The MO-218 plasmid was amplified by PCR using oligonucleotide primer 218-1 (CGCAAGCTTGAGAGCTCCGTTCCGCCACATGGTG-CGGTCTGTGGCCTGGG, SEQ ID NO: 12), which contains a Hind III site and nucleotides 2 through 23 of the MO-218 chitinase cDNA of SEQ ID NO: 1, and with complementary downstream primer T-END (GACTCTAGACTAGGTGCCTGAAGGCAAGTATG, SEQ ID NO: 13), which contains nucleotides 1164 through 1183 of MO-218, a stop codon and an XbaI site. The amplified DNA was purified by electrophoresis, digested with XbaI and HindIII, and cloned into the pRc/CMV vector (Invitrogen, San Diego, Calif.) previously cut with the same restriction enzymes. The junctions of the resulting clone was sequenced on a Model 373 (Applied Biosystems, Foster City, Calif.) and encoded the predicted engineered protein sequence, set forth in SEQ ID NO: 14.

All three plasmids were transiently transfected into COS cells by the DEAE transfection method [see, e.g., Sambrook et al., *Molecular Cloning: a Laboratory Manual*, 2d ed., Cold Spring Harbor, N.Y.: Cold Spring Harbor Laboratory (1989).). After three days at 37° C., media from cells was assayed for chitinase activity in vitro as described below in Example 8. Each culture produced significant chitinase activity (600–800 mU/m1min), and similar amounts were observed for each construct.

Recombinant human chitinase was purified as follows. Five days after transfection of COS cells with the pRc/CMV-MO-13B plasmid, conditioned media from the culture was harvested and diluted with an equal volume of water. The diluted conditioned media was applied to a Q-Sepharose Fast Flow column (Pharmacia Biotech, Uppsala, Sweden) which was pre-equilibrated in 25 mM Tris, 10 mM sodium chloride, 1 mM EDTA, at pH 8.0. Approximately 95 % of the chitinase activity flowed through and did not bind to the column. This Q-Sepharose flow through was adjusted to 1.2 M ammonium sulfate and applied to a Butyl-Sepharose 4 Fast Flow column (Pharmacia) which was pre-equilibrated in 25 mM Tris, 1.2 M ammonium sulfate, 1 mM EDTA, at pH 8.0. Protein was eluted using a reverse gradient of 1.2 M to 0 M ammonium sulfate in 25 mM Tris, pH 8.0. A single absorbance peak at 280 nm corresponding to the chitinase activity peak was eluted at low salt. This material was greater than 85 % pure as determined by SDS-PAGE and contained approximately 60% of the chitinase activity. The protein was then concentrated and buffer exchanged into 20 mM Tris, 150 mM sodium chloride, at pH 8.0 using a 10,000 MWCO membrane (Ultrafree 10K, Millipore Corp., Bedford, Mass.). This preparation was then tested for enzymatic and anti-fungal activity in vitro as described in Examples 8 and 9 below. The recombinant preparation had a chitotriosidase activity of 90 nm/min per mg protein.

B. Expression in CHO cells

The chitinase gene was inserted into pDEFI (the construction of which is described in Example 4 of U.S. application Ser. No. 08/847,218 filed May 1, 1997, incorporated herein by reference) by excising the 1.77 kb HindIII/XbaI fragment containing the full length chitinase gene from pRc/CMV/MO-13B and ligating the fragment with HindIII/XbaI-digested pDEF1, to create plasmid pDEFI/CTN.1. The 1.77 kb HindI/Xbal fragment containing the chitinase gene was also ligated into HindIII/XbaI-digested pHDEF1 to create plasmid pHDEF1/CTN.1. Plasmid pHDEF1 is the same as pDEF1 except for two differences: (1) in pHDEF1, a 2 kb EheI/SalI fragment derived from pCEP4 (Invitrogen, Carlsbad) containing a hygromycin resistance gene replaced the 19 bp PmeI/Sall fragment of pDEF1; (2) in pHDEF1, expression of the dihydrofolate reductase (DHPR) gene is controlled by a shortened SV40 promoter contained on a 120 bp NheI/Asp718 fragment that replaced the corresponding 212 bp NheV/Asp718 fragment of pDEF1. This 120 bp NheI/Asp718 fragment was prepared by first amplifying a 171 bp PCR fragment with oligonucleotide primer 94-26 (5'-TGATACGGTACCGCCCCATGGCTGACTA-3', SEQ ID NO: 16) (which contains a new Asp718 site), and primer 94-27 (5'-GCAAGTITGGCGCGAAAATCG-3', SEQ ID NO: 17), using as a template the DNA from pDC1 (described in Example 4 of U.S. application Ser. No. 08/847,218 filed May 1, 1997) that carries the SV40-DHFR cassette, and then digesting this 171 bp PCR fragment with NheI and Asp718.

The DHFR-negative Chinese hamster ovary (CHO) cell line DG44 was transfected with plasmid pDEF1/CTN.1 as described in Example 5 of U.S. application Ser. No. 08/847,218 filed May 1, 1997. The CHO cell line DG44 was also transfected with plasmid pHDEFl/CTN. 1, followed by selection using the following modified procedure. The cells were first selected for hygromycin resistance only, in media (DMEM/F-12 supplemented with 2–10% dialyzed FBS) containing 800 mg/liter of hygromycin (Calbiochem, San Diego) and also containing hypoxanthine and thymidine (which therefore made the media non-selective for the DHFR gene). After selecting transfectants that were resistant to hygromycin, the cells were further selected for expression of the DHFR gene by growing them in media lacking hypoxanthine and thymidine. Next, the DHFR-positive and hygromycin-resistant CHO cells were selected in media containing first 10 nM, then 20 nM, and finally 50 nM methotrexate, which resulted in selection of cells expressing higher levels of chitinase.

The supernatant from the pHDEF1/CTN.1 transfected CHO cells containing overexpressed recombinant human chitinase (rH-Chitinase) was purified as follows. In preparation for anion exchange chromatography, the supernatant was diluted 1:3 with 20 mM Tris, pH 7.0 (Buffer A). An anion exchange column, packed with Q-Sepharose Fast Flow Resin (Pharmacia Biotech Inc., Piscataway, N.J.), was equilibrated with Buffer A and loaded with 15L diluted supernatant per 1L resin. The rH-Chitinase was collected in the Flow Through from the Q-Sepharose column and adjusted to 5 % Polyethylene Glycol (PEG) 400 (Mallinckrodt Baker, Inc., Phillipsburg, N.J.), 30 mM sodium acetate, pH 4.3 in preparation for cation exchange chromatography. A cation exchange column, packed with CM-Sepharose Fast Flow Resin (Phannacia Biotech Inc., Piscataway, N.J.), was equilibrated with 30 mM sodium acetate, 5% PEG 400, pH 4.3 (Buffer B). The rH-Chitinase sample was loaded onto the CM-Sepharose column at 1 mg per mL resin, and rH-Chitinase was eluted from the column with 40 mM Tris, 5 % PEG 400, pH 7.5 (Buffer C). The rH-Chitinase sample was then prepared for hydrophobic interaction chromatography by adding $(NH_4)_2SO_4$ to 1.5M. A column packed with Macro-Prep Methyl H1C Support, (Bio-Rad Laboratories, Hercules, Calif.,) was equilibrated with 20 mM Tris, 5% PEG 400, pH 7.0 (Buffer D) containing 1.5M $(NH_4)_2SO_4$. The rH-Chitinase sample was loaded onto the Macro-Prep Methyl column at 1 mg per mL resin. The column was washed with Buffer D containing 1.1 M $(NH_4)_2SO_4$, and rH-Chitinase was eluted with Buffer D containing 0.2M $(NH_4)_2SO_4$. The purified eluate was exchanged into 150 mM NaCl, 20 mM Tris, pH 7.0 (Buffer E) by membrane filtration.

EXAMPLE 6

Production of Human Chitinase Analogs and Fragments

Recombinant techniques such as those described in the preceding examples may be used to prepare human chitinase polypeptide analogs or fragments. More particularly, polynucleotides encoding human chitinase are modified to encode polypeptide analogs of interest using well-known techniques, e.g., site-directed mutagenesis and polymerase chain reaction. C-terminal and N-terminal deletions may also be prepared by, e.g., deleting the appropriate portion of the polynucleotide coding sequence. See generally Sambrook et al., supra, Chapter 15. The modified polynucleotides are expressed recombinantly, and the recombinant polypeptide analogs or fragments are purified as described in the preceding examples.

Residues critical for human chitinase activity are identified, e.g., by homology to other chitinases and by substituting alanines for the native human chitinase amino acid residues. Cysteines are often critical for the functional integrity of proteins because of their capacity to form disulfide bonds and restrict secondary structure. To determine whether any of the cysteines in human chitinase are critical for enzymatic activity, each cysteine is mutated individually to a serme.

A 39 kDa C-terminally truncated fragment of the mature human chitinase protein was prepared as described above in Examples 3 and 5 by introduction of a stop codon after the codon for amino acid 373. This 39 kDa fragment lacked seventy-two C-terminal amino acid residues of the mature protein, including six cysteines, yet retained similar specific enzymatic activity compared to the full length recombinant human chitinase. This result indicates that the missing seventy-two C-terminal residues, including the six cysteines, are not required for enzymatic activity.

Further C-terminal deletions may be prepared, e.g., by digesting the 3' end of the truncated human chitinase coding sequence described in Example 3 with exonuclease m for various amounts of time and then ligating the shortened coding sequence to plasmid DNA encoding stop codons in all three reading frames. N-terminal deletions are prepared in a similar manner by digesting the 5' end of the coding sequence and then ligating the digested fragments into a plasmid containing a promoter sequence and an initiating methionine immediately upstream of the promoter site. These N-terminal deletion analogs or fragments may also be expressed as fusion proteins.

Alternatively, human chitinase polypeptide analogs may also be prepared by full or partial chemical peptide synthesis using techniques known in the art. [See, e.g., synthesis of IL-8 in Clark-Lewis et al., *J. Biol Chem.*, 266:23128–34 (1991); synthesis of IL-3 in Clarke-Lewis et al., *Science*, 231:134–139 (1986); and synthesis by ligation in Dawson et al., *Science*, 266:776–779 (1994).] Such synthetic methods also allow the selective introduction of novel, unnatural amino acids and other chemical modifications.

The biological activities, including enzymatic, antifungal, and extracellular matrix remodeling activities, of the human chitinase polypeptide analogs are assayed by art-recognized techniques, such as those described in Examples 8 to 14 below.

EXAMPLE 7

Preparation of Monoclonal Antibodies to Human Chitinase

The following two protocols (multiple challenge or single shot immunizations) may be used to generate monoclonal antibodies to human chitinase. In the first protocol, a mouse is injected periodically with recombinant human chitinase (e.g., 10–20 $\mu$g emulsified in Freund's Complete Adjuvant) obtained as described in any of Examples 3 through 6. The mouse is given a final pre-fusion boost of human chitinase in PBS, and four days later the mouse is sacrificed and its spleen removed. The spleen is placed in 10 ml serum-free RPMI 1640, and a single cell suspension is formed by grinding the spleen between the frosted ends of two glass microscope slides submerged in serum-free RPMI 1640, supplemented with 2 mM L-glutamine, 1 mM sodium pyruvate, 100 units/ml penicillin, and 100 $\mu$g/ml streptomycin (RPMI) (Gibco, Canada). The cell suspension is filtered through sterile 70-mesh Nitex cell strainer (Becton Dickinson, Parsippany, N.J.), and is washed twice by centrifuging at 200 g for 5 minutes and resuspending the pellet in 20 ml serum-free RPMI. Splenocytes taken from three naive Balb/c mice are prepared in a similar manner and used as a control. NS-1 myeloma cells, kept in log phase in RPMI with 11 % fetal bovine serum (FBS) (Hyclone Laboratories, Inc., Logan, Utah) for three days prior to fusion, are centrifuged at 200 g for 5 minutes, and the pellet is washed twice as described in the foregoing paragraph.

One$\times 10^8$ spleen cells are combined with $2.0 \times 10^7$ NS-1 cells and centrifuged, and the supernatant is aspirated. The cell pellet is dislodged by tapping the tube, and 1 ml of 37° C. PEG 1500 (50% in 75 mM Hepes, pH 8.0) (Boehringer Mannheim) is added with stirring over the course of 1 minute, followed by the addition of 7 ml of serum-free RPMI over 7 minutes. An additional 8 ml RPMI is added and the cells are centrifuged at 200 g for 10 minutes. After discarding the supernatant, the pellet is resuspended in 200 ml RPMI containing 15 % FBS, 100 $\mu$M sodium hypoxanthine, 0.4 $\mu$M aminopterin, 16 $\mu$M thymidine (HAT) (Gibco), 25 units/ml IL-6 (Boehringer Mannheim) and 1.5× $10^6$ splenocytes/ml and plated into 10 Corning flat-bottom 96-well tissue culture plates (Corning, Corning New York).

On days 2, 4, and 6, after the fusion, 100 $\mu$l of medium is removed from the wells of the fusion plates and replaced with fresh medium. On day 8, the fusion is screened by EUISA, testing for the presence of mouse IgG binding to human chitinase as follows. Immulon 4 plates (Dynatech, Cambridge, MA) are coated for 2 hours at 37° C. with 100 ng/well of human chitinase diluted in 25 mM Tris, pH 7.5. The coating solution is aspirated and 200 ul/well of blocking solution [0.5 % fish skin gelatin (Sigma) diluted in CMF-PBS] is added and incubated for 30 min. at 37° C. Plates are washed three times with PBS with 0.05% Tween 20 (PBST) and 50 $\mu$A culture supernatant is added. After incubation at 37° C. for 30 minutes, and washing as above, 50 $\mu$l of horseradish peroxidase conjugated goat anti-mouse IgG(fc) (Jackson ImmunoResearch, West Grove, Pa.) diluted 1:3500 in PBST is added. Plates are incubated as above, washed four times with PBST, and 100 $\mu$L substrate, consisting of 1 mg/ml o-phenylene diamine (Sigma) and 0.1 $\mu$l/ml 30% $H_2O_2$ in 100 mM Citrate, pH 4.5, are added. The color reaction is stopped after 5 minutes with the addition of 50 $\mu$l of 15 % $H_2SO_4$. $A_{490}$ is read on a plate reader (Dynatech). Selected fusion wells are cloned twice by dilution into 96-well plates and visual scoring of the number of colonies/well after 5 days. The monoclonal antibodies produced by hybridomas are isotyped using the Isostrip system (Boehringer Mannheim, Indianapolis, Ind.).

Alternatively, a second protocol utilizing a single-shot intrasplenic immunization may be conducted generally according to Spitz, *Methods Enzymol.*, 121:33–41 (1986). The spleen of the animal is exposed and injected with recombinant human chitinase (e.g., 10–20 $\mu$g in PBS at a concentration of about 0.02% to 0.04%, with or without an aluminum adjuvant) obtained as described in any of Examples 3 through 6, after which the spleen is returned to the peritoneal cavity and the animal is stitched closed. Three days later, the mouse is sacrificed and its spleen removed. A spleen cell suspension is prepared, washed twice with RPMI 1640. supplemented with 3% fetal calf serum (FCS), and resuspended in 25 ml of the same medium. Myeloma cells (NS-O) are collected at logarithmic growth phase, washed once and added to the spleen cell suspension in a 50 ml tube, at a ratio of 3:1 or 2:1 (spleen cells:myeloma cells). The mixture is pelleted at about 450 g (1500 rpm), the supernatant aspirated, and the pellet loosened by tapping the tube. Fusion is performed at room temperature by adding 1 ml of polyethylene glycol (PEG) 1500 over 1 minute, with constant stirring. The mixture is incubated for another minute, then 1 ml of warm RPMI (30 to 37° C.) is added over 1 minute followed by 5 ml RPMI over 3 minutes and another 10 ml RPMI over another 3 minutes. The cell suspension is centrifuged and resuspended in about 200 ml of HAT selective medium consisting of RPMI 1640 supplemented with 100 U/ml penicillin, 100 $\mu$g/ml streptomycin, 20% FCS, 100 mM hypoxanthine, 0.4 mM aminopterin and 16 mM thymidine. The cell suspension is dispensed in 1 ml volumes into tissue culture plates and incubated at 37° C. in a humid atmosphere with 5 % $CO_2$-95 % air for 8 to 10 days. Supernatants are aspirated and the cells are fed with 1 ml HAT medium per well, every 2 to 3 days according to cell growth. Supernatants of confluent wells are screened for specific antibodies and positive wells are cloned.

EXAMPLE 8

Catalytic Activity of Recombinant Chitinase

Chitotriosidase (chitinase) activity was measured using the fluorogenic substrate 4-methylumbelliferyl-$\beta$-D-N,N', N"-triacetylchitotriose (4 MU-chitotrioside, Sigma Chemical, St. Louis, Mo.) in McIlvain buffer (Hollak et al., supra). Ten $\mu$l samples of the recombinant product were combined with 10 itl bovine serum albumin (10 mg/ml), 15 µl fluorogenic substrate (2.71 mM), and 65 µl buffer (0.1M citric acid, 0.2M sodium phosphate, pH 5.2) in a total volume of 100 µl. Reactions were incubated at 37° C. for 15 minutes, then the reaction was stopped with the addition of 2 ml of 0.3M glycine/NaOH buffer (pH 10.6). The fluorescent cleavage product, 4-methylumbelliferone, was monitored with a fluorimeter (SLM-AMINCO Instruments, Inc., Rochester, N.Y.) at 450 nm. To obtain a standard curve, several substrate concentrations were combined with excess bacterial chitinase to ensure that substrate was completely cleaved. The known quantity of 4-MU was then correlated to the fluorescence signal from the fluorimeter and linear regression was used to determine a standard curve. The signal produced with diluted purified recombinant chitinase in the assay was then used to interpolate the nm quantity of substrate cleaved by the enzyme during the reaction time. This number was then divided by the concentration of protein to obtain the nm/min per mg protein (determined by $A_{280}$ and calculated molar extinction coefficient).

The chitotriosidase activity of the recombinant human chitinase produced in COS cells as described in Example SA was determined to be 90 nm/min per mg protein.

EXAMPLE 9

Anti-fungal Activity of Recombinant Chitinase In Vitro

In a preliminary experiment, recombinant human chitinase was tested for inhibition of fungal growth in vitro. The two fungi *Candida albicans* and *Aspergillus fumigatis* are serious pathogens for immunocompromised patients. Both Candida and Aspergillus were grown in RPMI growth media at 37° C. to approximately 10,000–50,000 colony forming units (CFU) per ml. Recombinant human chitinase (produced in COS cells as described in Example 5A) was added to cultures at 0, 2.8, 11.25, or 45 µg/ml. After 24 hours, fungal growth was assessed by turbidity of cultures. Under these non-physiological conditions in this assay, all cultures appeared to grow at comparable rates, independent of chitinase concentration. The concentration of fungi tested, however, is much higher than the fungal burden seen during fungal infection in vivo. Different results may be obtained under different conditions, e.g., with a lower fungal burden, or when human chitinase is tested in combination with other anti-fungal agents. Chitinase is also expected to be more effective in Wvo under physiological conditions.

In additional experiments, the anti-fungal activity of recombinant human chitinase (produced in COS cells as described in Example 5A) was evaluated in an agar diffusion assay, in a broth assay according to National Committee on Clinical Laboratory Standards, and in a cell wall inhibition assay according to Selitrennikoff, *Antimicrob. Agents Chemother.*, 23:757–765 (1983).

In the agar diffusion assay, approximately $1 \times 10^6$ cells/ml of *Candida albicans* (ATCC no. 90028) inoculated into 1.5% agar (RPMI 1640 media buffered with 2-(N-morpholino)propanesulfonic acid (MOPS), pH 7.0. A disk containing 50 µg of the sample (A: recombinant human chitinase, B: buffer control, C: control protein, D: a bacterial lysate with chitinase activity, or a known anti-fungal agent) was placed on the agar, and the zone of growth inhibition was measured. Results are shown in Table 1 below.

TABLE 1

| Sample[a] 50 µg/disk | *Candida albicans* Growth[b] | *Aspergillus fumigatus* Growth |
|---|---|---|
| A: rH-Chitinase | + | + |
| B: Buffer Control | + | + |
| C: Control Protein | + | + |
| D: Bacterial lysate with chitinase activity | + | +[c] |
| amphotericin B (400 ng/disk) | − | − |

[a]Samples: A = rH-Chitinase prepared from COS cells according to Example 5A, in 150 mM NaCl, 1 mM EDTA, 20 mM Tris, pH 7.5; B = buffer (150 mM NaCl, 1 mM EDTA, 20 mM Tris, pH 7.5); C = inactive protein PAF-AH (diluted from a 2 mg/ml stock solution); D = *Serratia marcescens* lysate (SIGMA #C-7809) with chitinase activity.
[b]Growth Scoring Key: (+) = Normal growth, no inhibition of growth observed; (−) = Inhibited fungal growth, zone of inhibition is observed.
[c]Sample D stimulated the growth of *Aspergillus fumigatus*.

In the broth assay, 50 µg/ml of the sample (A: recombinant human chitinase, B: buffer control, C: control protein, D: a bacterial lysate with chitinase activity, or a known anti-fungal agent) was added with a certain concentration of the test fungal organism to RPMI 1640 media buffered with MOPS, pH 7.0. The samples were incubated at 35° C., with shaking at 120 rpm, for 48 hours, and then growth was evaluated by measuring the turbidity of the suspension. The approximate concentrations of the test fungi were as follows: $2.5 \times 10^4$ cells/ml of *Candida albicans* (ATCC no. 90028); $5 \times 10^4$ cells/ml of *Candida albicans*-polyene resistant (ATCC no. 38247); 1 x 104 cells/ml of *Aspergillus fumigatus* (ATCC no. 16424); $1 \times 10^4$ cells/ml of *Neurospora crassa* (ATCC no. 18889); and $1 \times 10^4$ cells/ml of *Saccharomyces cerevisiae* (ATCC no. 26108). Results are shown in Table 2 below.

TABLE 2

| Sample[a] (50 µg/ml) | *Candida albicans* Growth[b] | *C. albicans*-polyene resistant Growth | *Aspergillus fumigatus* Growth | *Neurospora crassa* Growth | *Saccharomyes cerevisiae* Growth |
|---|---|---|---|---|---|
| A: rH-Chitinase | 2 | 2 | 3 | 4 | 2 |
| B: Buffer Control | 2 | 2 | 4 | 4 | 2 |
| C: Control Protein | 4 | 3 | 4 | 4 | 4 |
| D: Bacterial lysate with chitinase activity | 4 | 4 | 4 | 4 | 4 |
| $IC_{90}$[c] of amphotericin B | 0.5 µg/ml | >16 µg/ml | 2 µg/ml | 0.5 µg/ml | 1 µg/ml |
| $IC_{50}$[d] of fluconazole | 0.5 µg/ml | 16 µg/ml | NA | 8 µg/ml | 4 µg/ml |

TABLE 2-continued

| Sample[a] (50 μg/ml) | Candida albicans Growth[b] | C. albicans-polyene resistant Growth | Aspergillus fumigatus Growth | Neurospora crassa Growth | Saccharomyes cerevisiae Growth |
|---|---|---|---|---|---|
| IC$_{50}$ of 5-fluorocytosine | 2 μg/ml | 0.06 μg/ml | 16 μg/ml | >64 μg/ml | 0.125 μg/ml |
| IC$_{50}$ of miconazole | NA | 2 μg/ml | 0.5 μg/ml | NA | NA |

[a]Samples: A = rH-Chitinase prepared from COS cells according to Example 5A, in 150 mM NaCl, 1 mM EDTA, 20 mM Tris, pH 7.5; B = buffer (150 mM NaCl, 1 mM EDTA, 20 mM Tris, pH 7.5); C = inactive protein PAF-AH (diluted from a 2 mg/ml stock solution); D = *Serratia marcescens* lysate (SIGMA #C-7809) with chitinase activity.
[b]Growth Scoring Key: 0 = No fungal growth; 1 = growth is 25% of control; 2 = growth is 50% of control; 3 = growth is 75% of control; 4 = growth equivalent to control; 5 = growth is greater than control.
[c]IC$_{90}$: the lowest concentration at which a compound inhibits the growth of an organism by at least 90%; equivalent to at least a score of 0.
[d]IC$_{50}$: the lowest concentration at which a compound inhibits the growth of an organism by at least 50%; equivalent to at least a score of 2.

The os-1 whole cell assay, which identifies inhibitors of fungal cell wall biosynthesis, was conducted essentially according to Selitrennikoff, supra, using an inoculum of 1.5×10$^5$ protoplasts/ml embedded in agar (Vogel's Medium N, 7.5% sorbitol, 1.5 % sucrose, 10 μg/ml nicotiniamide and 1 % agar) incubated at 25° C. for 72 hours. The cultures were monitored for changes in growth and morphology after disks containing 50 μg of the sample (A: recombinant human chitinase, B: buffer control, C: control protein, D: a bacterial lysate with chitinase activity, or a known anti-fungal agent) were placed on the agar medium. The os-1 cell is a mutant strain of *Neurospora crassa* that grows as protoplasts without cell walls when incubated under certain conditions at 37° C., but regenerates a cell wall under the appropriate conditions when the temperature is shifted to about 22° C. Samples that inhibit growth are considered fungal growth inhibitors and samples that prevent cell wall regeneration, but do not kill the cells, are considered cell wall-specific inhibitors. Results are shown in Table 3 below.

TABLE 3

| Sample[a] (50 μg/disk) | Cell Growth/ Morphology[b] | Cell Wall Regenertion[c] |
|---|---|---|
| A: rH-Chitinase | + protoplasts | − 10 mm[d] |
| B: Buffer Control | + protoplasts | − 5 mm[d] |
| C: Protein Control | + hyphae | + |
| D: Bacterial lysate with chitinase activity | + protoplasts | − 7 mm[d] |
| nikkomycin Z (1 μg/disk) | + protoplasts | − 30 mm[d] |
| amphotericin B (400 ng/disk) | − cell debris | + 10 mm[e] |

[a]Samples: A = rH-Chitinase prepared from COS cells according to Example 5A, in 150 mM NaCl, 1 mM EDTA, 20 mM Tris, pH 7.5; B = buffer (150 mM NaCl, 1 mM EDTA, 20 mM Tris, pH 7.5); C = inactive protein PAF-AH (diluted from a 2 mg/ml stock solution); D = *Serratia marcescens* lysate (SIGMA #C-7809) with chitinase activity.
[b]Scoring Key for fungal growth: (+) = Normal growth, no inhibition of growth observed; (−) = Inhibited fungal growth, zone of inhibition is observed.
[c]Scoring Key for cell-wall regeneration: (+) = Normal cell-wall regeneration; (−) = Inhibited cell-wall regeneration.
[d]Radial measurements of inhibited cell-wall regeneration from center of disk.
[e]Radial measurement of inhibited growth from center of disk.

The results of these assays showed that the chitinase sample was a cell wall specific inhibitor in the os-1 whole cell assay and was mildly anti-fungal in the broth assay.

EXAMPLE 10

Anti-fungal Activity of Recombinant Chitinase In Vivo in Mice

The pharmacokinetics of recombinant human chitinase in mice were determined as follows. Female Balb/c mice, 6–8 weeks old, were injected intravenously in the tail vein with 0.5 mg/kg, 5.0 mg/kg and 50 mg/kg recombinant human chitinase. For each dose, mice were terminally bled at 0.01, 0.25, 1, 8 and 24 hours after injection (2 animals were used per time point per dosage). Serum samples were then assayed for chitinase activity and concentration. Results are shown in Table 4 below.

TABLE 4

| Dose (mg/kg) | AUC (μg/ml/h) | Vss (ml/kg) | cL (ml/h/kg) | MRT (h) | half-life (h) | Cmax (μg) |
|---|---|---|---|---|---|---|
| 0.5 | 31.24 | 12.03 | 16.01 | 0.75 | 0.74 | 22.30 |
| 5.0 | 278.50 | 13.61 | 17.95 | 0.76 | 1.38 | 162.84 |
| 50.0 | 2505.83 | 52.92 | 19.95 | 2.65 | 2.33 | 1179.19 |

AUC: area under curve to time infinity
Vss: steady state volume of distribution
cL: clearance
MRT: total body mean residence time
Cmax: peak serum concentration Several animal models have been developed for testing efficacy of anti-fungal compounds [see Louie et al., *Infect. Immun.*, 62: 2761–2772, 1994; Kinsman et al., *Antimicrobial Agents and Chemotherapy*, 37: 1243–1246, 1993; Nakajima et al., *Antimicrobial Agents and Chemotherapy* 39: 1517–1521, 1995; Tonetti et al., *Eur. J. Immunol.*, 25:1559–1565 (1995); Denning and Stevens, *Antimicrob. Agents Chemother.*, 35:1329–1333 (1991); see also Stevens, J. Mycol. Med., 6(suppl.I):7–10 (1996)]. Briefly, the animal host is infected with the fungi, varying doses of chitinase are administered to the animals, and their survival is measured over time. The experiments are performed using chitinase as the sole therapeutic agent, or with a combination of conventional anti-fungal agents such as Amphotericin B and fluconazole to determine if the chitinase improves the efficacy of such compounds. Specifically, acute systemic candidiasis is achieved in mice by intraperitoneal or intravenous challenge of 10×10$^6$ CFU *Candida albicans*. The therapeutic agents are administered before or at 1 to 5 hours after challenge, and the number of survivors is determined after five days. In addition, the mice can be sacrificed and fungal load can be determined in specific organs such as brain, kidney, lung, liver and spleen. Alternatively, the mice are challenged with lower doses of fungi, e.g., Aspergillus ($8-10 \times 10^6$ CFU) or Candida ($1 \times 10^6$ CFU), in which case survival can be measured at more distant time points, e.g., 45 days. The long term fungicidal/fungistatic activity of chitinase alone or with another anti-fungal drug may be evaluated by continuing therapy for a week or more, e.g., 11 days, and following the animals over several weeks, e.g., 18 days to one month. Effective anti-fungal agents enhance the long term survival of animals and reduce fungal load in blood and organs.

EXAMPLE 11

Activity of Chitinase In Vivo in a Rabbit Model of Invasive Aspergillosis

The efficacy of chitinase, alone or in combination with other conventional anti-fungal agents, is assessed in an immunosuppressed rabbit model of invasive aspergillosis which has been used for over ten years to evaluate a variety of anti-fungal therapies. See, e.g., Andriole et al., *Clin. Infect. Dis., b 14*(Suppl. 1):S134–S138 (1992). The study is conducted generally according to Patterson et al., Antimicrob. Agents Chemother., 37:2307-2310 (1993) or George et al., *J. Infect. Dis.*, 168:692–698 (1993). Briefly, on day one the rabbits are given cyclophosphamide (200 mg) intravenously to render them leukopenic, followed by triamcinolone acetonide (10 mg) subcutaneously each day for the duration of the experiment. On day two, 24 hours after immunosuppression, the animals are challenged intravenously with about $10^6$ (lethal challenge) or about $10^5$ (sublethal challenge) *A. fumigatus* conidia. Anti-fungal therapy (chitinase alone, or in combination with other conventional anti-fungal agents, e.g., amphotericin B, fluconazole, or 5-fluorocytosine) is initiated at 24 hours after challenge or 48 hours before challenge (for prophylaxis) and is continued for 5 to 6 days or until death. Exemplary doses of conventional anti-fungal agents are 1.5 or 0.5 mg/kg/day intravenous amphotericin B, 60 or 120 mg/kg/day oral fluconazole and 100 mg/kg/day oral 5-fluorocytosine. Control rabbits are not treated with any anti-fungal agent.

At autopsy or death, semiquantitative fungal cultures and histopathologic examination are conducted on the liver, spleen, kidneys, lungs and brain. Cultures of the heart, urine and blood may also be performed. Blood samples are obtained at intervals and assayed for white blood cell counts and circulating Aspergillus carbohydrate antigen using an EUISA assay. The effect of treatment with the test drug is evaluated on three endpoints: reduction in mortality rate, reduction in number of Aspergillus organisms cultured from target organs (fungal burden), and reduction in level of circulating Aspergillus antigen. Effective anti-fungal agents reduce mortality and/or fungal load.

Alternatively, pulmonary aspergillosis may be evaluated in this model generally according to Chilvers et al., *Mycopathologia*, 108:163–71 (1989), in which the immunosuppressed rabbits are challenged with intratracheal instillation of *Aspergillus fumigatus* conidia, followed by bronchoalveolar lavage on days 1, 2, 4, 7 and 10 following challenge; fungal culture, chitin assay, white cell counts and histopathology are performed on the lavage fluids to determine infective load within the lung. Effective fungal agents reduce the infective load or inflammation within the lung.

EXAMPLE 12

Activity of Chitinase In Vivo in a Rabbit Model of Disseminated Candidiasis

The efficacy of chitinase, alone or in combination with other conventional anti-fungal agents, is assessed in a rabbit model of disseminated candidiasis generally according to Rouse et al., *Antimicrob. Agents Chemother.*, 36:56–58 (1992). New Zealand white rabbits are infected systemically with about $3 \times 10^6$ *Candida albicans* blastospores. Antifungal therapy is initiated 48 hours after challenge with Candida (or before challenge for prophylaxis) and is continued for, e.g., four days. Surviving animals are sacrificed, and fungal cultures are performed on the aortic valve with attached vegetation, lung, kidney and spleen. Fungal cultures and histopathological examination may also be performed on these and other organs, such as liver, brain, and heart. Urine and blood cultures may also be done. The effect of the anti-fungal therapy on mortality and circulating or tissue fungal burden is determined.

Bayer et al., *Antimicrob. Agents Chemother.*, 19:179–184 (1981), in which rabbits are inoculated intraperitoneally with about $5 \times 108$ CFU *Candida albicans*. A saline peritoneal aspirate is obtained and cultured from each animal four days after intraperitoneal inoculation, and animals with a positive fungal culture aspirate are randomly assigned to control or treatment groups. Anti-fungal treatment is begun seven days after challenge. The eyes of all rabbits are evaluated using indirect ophthalmoscopy, as disseminated candidiasis may result in Candida endophthalmitis. Animals are sacrificed at 7, 11 and 14 days after initiation of therapy and their abdomens inspected for evidence of peritonitis and intraabdominal abscess formation. Eyes are examined for macroscopic lesions. Tissue samples from peritoneal abscesses, all other visible abscesses, kidneys, livers, spleens and ocular structures are weighed, homogenized in brain heart infusion broth, serially diluted and cultured to determine the CFU per gram of tissue. Renal and peritoneal abscesses are also fixed in 10% neutral formaldehyde and examined for histopathology. Sections are stained with periodic acid-Schiff reagent to determine the fungal burden and fungal morphology. Effect of the test drugs on improving survival and reducing fungal burden is evaluated.

EXAMPLE 13

Activity of Chitinase In Vivo in a Rabbit Model of Fungal Endophthalmitis

The efficacy of chitinase, alone or in combination with other conventional anti-fungal agents, is assessed in a rabbit model of Candida endophthalmitis, generally according to Park et al., *Antimicrob. Agents Chemother.*, 39:958–963 (1995). Briefly, New Zealand albino rabbits, 2 to 2.5 kg, are infected with an intravitreal inoculation of about 1,000 CFU of *Candida albicans*. Endophthalmitis is confirmed 5 days after inoculation by indirect ophthalmoscopy, and is defined as moderate to severe vitreous haze with partial or complete obscuration of greater than 50% of the retinal and choroidal vasculature. The vitreous turbidity is graded on a scale, and the fundus appearance may be graded and documented by fundus photography. The rabbits are then randomized to the following treatment conditions: chitinase alone for 2 to 4 weeks, a combination of chitinase and another conventional anti-fungal agent (e.g., amphotericin B, fluconazole or 5-fluorocytosine) for 2 to 4 weeks, or no treatment (control). Exemplary doses of conventional anti-fungal agents are 80 mg/kg/day of oral fluconazole and 100 mg/kg every 12 hours of oral 5-fluorocytosine.

The treatment effect is assessed at 2 and 4 weeks after therapy by indirect ophthalmoscopy, quantitative fungal culture, and histopathology. For quantitative fungal culture, the eyes are dissected and weighed, and a weighed fraction of each sample is homogenized and cultured on brucella agar-5 % horse blood plates for 48 hours at 35° C. in 5 to 10% $CO_2$. The homogenized sample may also be diluted 10- or 100-fold with sterile saline before plating. The colonies are counted and the total CFU in the eye calculated on the basis of the growth yielded from the measured fractions of sample. Treatment effect is assessed in terms of a reduction in the total intraocular fungal burden. For histopathology, representative eyes are removed, fixed in formalin, embedded in plastic, and sliced into 5 μm sections. The sections are stained with hematoxylineosin or Gomori's methenamine silver stain and examined by light microscopy for inflammation, fibrous organization and fungal elements. The effect of the anti-fungal agents on reducing mortality, reducing fungal load, or reducing the inflammation associated with fungal infection, is evaluated.

Alternatively, a rabbit model of Aspergillus endophthalmitis may be used generally according to Jain et al., *Doc. Ophthalmol.*, 69:227–235 (1988). Briefly, New Zealand white rabbits are inoculated in one eye with about forty spores of *Aspergillus fumigatus*. Their contralateral (control) eyes receive a similar but sterile inoculum. After treatment with the test drug (chitinase alone, or chitinase in combination with another agent), the rabbits' eyes may be evaluated for clinical appearance, electroretinogram waveforms, indirect ophthalmoscopy, quantitative fungal culture, and histopathology. Clinically evident endophthalmitis typically develops within three to seven days after inoculation.

EXAMPLE 14

Activity of Chitinase In Vivo in a Rabbit Model of Fungal Endocarditis

The efficacy of chitinase, alone or in combination with other conventional anti-fungal agents, is assessed in a rabbit model of *Candida endocarditis* generally according to Witt and Bayer, *Antimicrob. Agents Chemother.*, 35:2481–2485 (1991). See also Longman et al., *Rev. Infect. Dis.*, 12(Suppl. 3):S294–298 (1990). Sterile thrombotic endocarditis is produced in New Zealand white rabbits by transaortic valvular placement of a sterile polyethylene catheter (internal diameter, 0.86 mm), which remained in place for the duration of the study. Infective endocarditis is then established 48 hours after catheterization by intravenous injection of about $2 \times 10^7$ *C. albicans* blastospores. Alternatively, *C. parapsilosis* may be used. Anti-fungal therapy (chitinase or chitinase in combination with another conventional anti-fungal agent) is initiated either 24 hours before or 24 to 60 hours after fungal challenge. Therapy is continued daily for 9 or 12 days. Exemplary doses of conventional anti-fungal agents are 1 mg/kg/day intravenous amphotericin B, 50 mg/kg/day or 100 mg/kg/day intravenous or intraperitoneal fluconazole. Control rabbits are given no anti-fungal agent. At sacrifice, hearts are removed and the position of the indwelling catheter verified. Cardiac vegetations from each animal are removed, pooled, weighed and homogenized in 1 ml of sterile saline. The homogenate is serially diluted and quantitatively cultured on yeast potassium dextrose agar at 35° C. for 48 hours. Culture-negative vegetations are considered to contain less than 2 $\log_{10}$ CFU/gram on the basis of average vegetation weight.

Numerous modifications and variations of the above-described invention are expected to occur to those of skill in the art. Accordingly, only such limitations as appear in the appended claims should be placed thereon.

What is claimed is:

1. A method of reducing the amount of a non-chitinase anti-fungal agent needed to exert an anti-fungal activity in a subject, comprising administering to said subject an amount of a chitinase comprising SEQ ID NO: 2 or allelic variants thereof effective to improve the anti-fungal activity of said non-chitinase anti-fungal agent, said non-chitinase anti-fungal agent being selected from the group consisting of amphotericin B and azole derivatives.

2. The method of claim 1 wherein the non-chitinase anti-fungal agent is amphotericin B.

3. The method of claim 1 wherein the non-chitinase anti-fungal agent is itraconazole.

4. The method of claim 1 wherein the subject is suffering from a fungal infection selected from the group consisting of candidiasis, aspergillosis, coccidioidomycosis, blastomycosis, paracoccidioidomycosis, histoplasmosis, cryptococcosis, chromoblastomycosis, sporotrichosis, mucormycosis, dermatophytoses and Pneumocystis infections.

5. The method of claim 1 wherein the fungal infection involves Candida species.

6. The method of claim 1 wherein the fungal infection involves Aspergillus species.

7. The method of claim 1 wherein the fungal infection involves Cryptococcus species.

8. The method of claim 1 wherein the subject is suffering from a fungal infection involving a fungal species whose growth is not effectively inhibited by contact with human chitinase alone.

* * * * *

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

<u>Title page,</u>
Item [56], References Cited, please add the following application:
-- Allison *et al.*, Serial No. 09/409,918 filed 09/30/99 --.
OTHER PUBLICATIONS, replace "R.G. Boot et al.," with -- R.G. Boot *et al.*, --; replace "A.M. Pope et al.," with -- A.M. Pope *et al.*, --; replace "D.A.L. Davies et al.," with -- D.A.L. Davies *et al.*, --; replace "G.H. Renkema et al.," with -- G.H. Renkema *et al.*, --; replace "Altschul et al.," with -- Altschul *et al.*, --; replace "Andriole et al.," with -- Andriole *et al.*, --; replace "Argueso et al.," with -- Argueso *et al.*, --; replace "Bayer et al.," with -- Bayer *et al.*, --; replace "Bitter et al.," with -- Bitter *et al.*, --; replace "Boot et al.," with -- Boot *et al.*, --; replace "Chilvers et al.," with -- Chilvers *et al.*, --; replace "Clark-Lewis et al.," with -- Clark-Lewis *et al.*, --; replace "Clark-Lewis et al.," with -- Clark-Lewis *et al.*, --; replace "Clarke et al.," with -- Clarke *et al.*, --; replace "Dawson et al.," with -- Dawson *et al.*, --; replace "DeSouza et al.," with -- DeSouza *et al.*, --; replace "Escott et al.," with -- Escott *et al.*, --; replace "Falcone et al.," with -- Falcone *et al.*, --; replace "Feldmann et al.," with -- Feldmann *et al.*, --; replace "George et al.," with -- George *et al.*, --; replace "Georgopapadakou et al.," with -- Georgopapadakou *et al.*, --; replace "Gillis et al.," with -- Gillis *et al.*, --; replace "Hakala et al.," with -- Hakala *et al.*, --; replace "Heitz et al.," with -- Heitz *et al.*, --; replace "Hollak et al.," with -- Hollak *et al.*, --; replace "Jain et al.," with -- Jain *et al.*, --; replace "Johansen et al.," with -- Johansen *et al.*, --; replace "Jones et al.," with -- Jones *et al.*, --; replace "Kinsman et al.," with -- Kinsman *et al.*, --; replace "Krishnan et al.," with -- Krishnan *et al.*, --; replace "Lin et al.," with -- Lin *et al.*, --; replace "Longman et al.," with -- Longman *et al.*, --; replace "Louie et al.," with -- Louie *et al.*, --; replace "Nakajima et al.," with -- Nakajima *et al.*, --; replace "Orr-Weaver et al.," with -- Orr-Weaver *et al.*, --; replace "Overdijk et al.," with -- Overdijk *et al.*, --; replace "Park et al.," with -- Park *et al.*, --; replace "Patterson et al.," with -- Patterson *et al.*, --; replace "Price et al.," with -- Price *et al.*, --; replace "Price *et al.*, Interleukins-2" with -- Price *et al.*, Interleukin-2 --; replace "Recklies et al.," with -- Recklies *et al.*, --; replace "Renkema et al.," with -- Renkema *et al.*, --; replace "Rouse et al.," with -- Rouse *et al.*, --; replace "Semino et al.," with -- Semino *et al.*, --; replace "Sleep et al.," with -- Sleep *et al.*, --; replace "Stearns et al.," with -- Stearns *et al.*, --; replace "Tjoelker et al.," with -- Tjoelker *et al.*, --; replace "Tonnetti et al.," with -- Tonnetti *et al.*, --; replace "Witt et al.," with -- Witt *et al.*, --; replace "Davies et al.," with -- Davies *et al.*, --; replace "Denning et al.," with -- Denning *et al.*, --; replace "Henrissat et al.," with -- Henrissat *et al.*, --; replace "Renkema et al.," with -- Renkema *et al.*, --; replace "Rex et al.," with -- Rex *et al.*, --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 1,
Lines 31-33, replace "Canrda, Aspergillus, Cryptococcus, Histoplasma, Coccidioides and Pneumocystis" with -- *Candida, Aspergillus, Cryptococcus, Histoplasma, Coccidioides and Pneumocystis* --
Line 52, replace "268.25803-25810" with -- 268:25803-25810 --.
Line 64, replace "Athritis" with -- *Arthritis* --.

Column 5,
Line 5, replace "C.hitinase," with -- Chitinase, --.
Lines 58 and 63, replace "in vivo" with -- *in vivo* --.

Column 6,
Line 11, replace "terbinafme" with -- terbinafine --.
Line 42, replace "Pa." with -- PA --.
Line 42, replace "1 gg/kg" with -- 1 $\mu$g/kg --.

Column 7,
Line 1, replace "extraceflular" with -- extracellular --.
Lines 22 and 25, replace "e.g.," with -- *e.g.*--.
Line 23, replace "Dec. 21, 1995." with -- 21 December 1995. --.
Line 26, replace "Hollak et al." with -- Hollak *et al.* --.
Line 55, replace "in vitro" with -- *in vitro* --.
Line 57, replace "in vivo" with -- *in vivo* --.
Line 59, replace "Candida" with -- *Candida* -- (both occurrences).
Lines 66-67, replace "Tjoelker et al." with -- Tjoelker *et al.* --.

Column 8,
Lines 5 and 7, replace "Calif.)" with -- CA) --.
Line 15, replace "Altschul et al." with -- Altschul *et al.* --.
Line 19, replace "Hakala et al., supra)," with -- Hakala *et al., supra*), --.
Line 20, replace "DeSouza et al., supra)," with -- De Souza *et al., supra*), --.
Line 22, replace "Chelonus" with -- *Chelonus* --.
Line 23, replace "X771 11)," with -- X77111), --.
Line 23, replace "Nicotiana" with -- *Nicotiana* --.
Line 24, replace "Serratia" with -- *Serratia* --.
Line 30, replace "Jun." with -- June --.
Line 33, replace "Md." with -- MD --.
Line 41, replace "aminoterminal" with -- amino-terminal --.
Lines 42-43, replace "Renkema et al., supra.:" with -- Renkema *et al., supra.* --.
Line 43, replace "Renkema et al." with -- Renkema *et al.* --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 8 (cont'd),
Line 46, replace "Boot et al., supra," with -- Boot *et al., supra,* --.
Line 49, replace "Boot et al." with -- Boot *et al.* --.
Line 66, replace "Jun. 7, 1996" with -- June 7, 1996 --.

Column 9,
Line 2, replace "Md." with -- MD --.
Line 6, replace "compared-with" with -- compared with --.
Line 19, replace "Calif.)" with -- CA) --.
Line 61, replace "by-MO-218." with -- by MO-218. --.

Column 10,
Lines 1 and 2, replace "Wilcox et al." with -- Wilcox *et al.* --.
Line 4, replace "Salmonella typhimurium" with -- *Salmonella typhimurium* --.
Line 4, replace "EcoRl/Xbal" with -- *Eco*RI/*Xba*I --.
Line 14, replace "EcoRl" with -- *Eco*Rl --.
Line 17, replace "Xbal" with -- *Xba*l --.
Line 19, replace "EcoRl and Xbal" with -- *Eco*Rl and *Xba*l --.
Line 20, replace "Mass.)" with -- MA) --.
Line 23, replace "Xbal" with -- *Xba*l --.
Line 24, replace "HindIII" with -- *Hind*III --.
Lines 36-37, 42 and 43, replace "E. coli" with -- *E. coli* --.
Line 65, replace "e.g.," with -- *e.g.,* --.

Column 11,
Line 8, replace "[Kujan" with -- [Kurjan --.
Line 9, replace "30.933-943" with -- 30:933-943 --.
Line 9, replace "1982))." with -- (1982)]. --.
Line 14, replace "[Meth. Enz.," with -- [*Meth. Enz.,* --.
Line 15, replace "Calif." with -- CA --.
Line 31, replace "e.g." with -- *e.g.* --.
Line 31, replace "[Stearns et al.," with -- [Stearns *et al.,* --.
Line 32, replace "supra," with -- *supra,* --.
Line 34, replace "[Price et al.," with -- [Price *et al.,* --.
Line 39, replace "Bfitter et al.," with -- [Bitter *et al.,* --.
Line 47, replace "Gillis et al." with -- Gillis *et al.* --.
Line 54, replace "[Orr-Weaver et al.," with -- [Orr-Weaver *et al.,* --.
Line 58, replace "GALA," with -- GAL4, --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 11 (cont'd),
Line 60, replace "[Sleep et al.," with -- [Sleep *et al.,* --.
Line 60, replace "8:4246 (1990)]." with -- 8:42-46 (1990)]. --.
Line 63, replace "Hansenula" with -- *Hansenula* --.
Line 64, replace "Aspergillus" with -- *Aspergillus* --.
Line 66, replace "[e.g." with -- [*e.g.* --.
Line 66, replace "Falcone et al.," with -- Falcone *et al.* --.
Line 67, replace "Plasmnd" with -- *Plasmid* --.

Column 12,
Lines 5 and 44, replace "e.g.," with -- *e.g.,* --.
Line 10, replace "cerevsiae" with -- *cerevisiae* --.
Line 30, replace "Hind III" with -- *Hind*III --.
Line 35, replace "XbaI" with -- *Xba*I --.
Line 37, replace "XbaI and HindIII" with -- *Xba*I and *Hind*III --.
Lines 38 and 41, replace "Calif.)" with -- CA) --.
Lines 44-45, replace "Sambrook et al." with -- Sambrook *et al.* --.
Line 46, replace "N.Y.;" with -- New York; --.
Line 47, replace "(1989).)." with -- (1989)]. --.
Line 48, replace "in vitro" with -- *in vitro* --.
Line 50, replace "(600-800 mU/mlmin)," with -- (600-800 mU/ml/min), --.

Column 13,
Line 7, replace "Mass.)." with -- MA). --.
Line 8, replace "in vitro" -- *in vitro* --.
Line 13, replace "U.S. application" with -- U.S. Application --.
Line 15, replace "HindIII/XbaI" with -- *Hind*III/*Xba*I --.
Line 17, replace "HindIII/XbaI-digested" with -- *Hind*III/*Xba*I-digested --.
Line 19, replace "HindI/XbaI" with -- *Hind*III/*Xba*I --.
Line 25, replace "PmeI/SalI" with -- *Pme*I/*Sal*I --.
Line 26, replace "(DHPR)" with -- (DHFR) --.
Lines 28 and 30, replace "NheI/Asp718" with -- *Nhe*I/*Asp*718 --.
Line 29, replace "NheV/Asp718" with -- *Nhe*I/*Asp*718 --.
Line 33, replace "Asp718" with -- *Asp*718 --.
Line 34, replace "(5'-GCAAGTITGGCGAAATCG-3'," with
-- (5'-GCAAGTTTGGCGAAATCG-3', --.
Lines 36 and 41, replace "application" with -- Application --.
Line 38, replace "NheI and Asp718." with -- *Nhe*I and *Asp*718. --.
Line 43, replace "pHDEFI/CTN. 1," with -- pHDEFI/CTN.1, --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 14,
Line 5, replace "Phannacia" with -- Pharmacia --.
Line 14, replace "Calif.,)" with -- CA) --.
Lines 33, 35, 42 and 61, replace "e.g.," with -- *e.g.*, --.
Lines 36-37, replace "Sambrook et al., supra," with -- Sambrook *et al., supra,* --.
Line 49, replace "serme." with -- serine --.
Line 63, replace "m" with -- III --.

Column 15,
Line 8, replace "[See, e.g.," with -- [See, *e.g.*, --.
Line 9, replace "Clark-Lewis et al.," with -- Clark-Lewis *et al.*, --.
Line 10, replace "Clarke-Lewis et al.," with -- Clarke-Lewis *et al.*, --.
Lines 11-12, replace "Dawson et al.," with -- Dawson *et al.*, --.
Line 30, replace "(e.g.," with -- (*e.g.*, --.
Line 42, replace "N.J.)," with -- New Jersey), --.
Line 51, replace "Onex10$^8$" with -- One x 10$^8$ --.

Column 16,
Line 1, replace "EUISA," with -- ELISA, --.
Line 9, replace "50 $\mu$A" with -- 50 $\mu$l --.
Line 12, replace "Pa.)" with -- Pennsylvania) --.
Line 23, replace "Ind.)." with -- IN). --.
Line 28, replace "(e.g.," with -- (*e.g.*, --.
Line 35, replace "1640.supplemented" with -- 1640 supplemented --.
Line 66, replace "Mo.)" with -- MO) --.
Lines 66-67, replace "Hollak et al., supra" with -- Hollak *et al., supra* --.

Column 17,
Line 1, replace "10 itl" with -- 10 $\mu$l --.
Line 22, replace "Example SA" with -- Example 5A --.
Lines 26-27, replace "In Vitro" with -- *In Vitro* --.
Line 30, replace "in vitro" with -- *in vitro* --.
Line 33, replace "Candida and Aspergillus" with -- *Candida* and *Aspergillus* --.
Line 43, replace "in vivo" with -- *in vivo* --.
Line 44, replace "e.g.," with -- *e.g.*, --.
Line 47, replace "in Wvo" with -- *in vivo* --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 18,
Line 46, replace "1 x 104" with -- $1 \times 10^4$ --.

Column 19,
Lines 20, 30 and 66, replace "os-1" with -- *os-1* --.
Line 22, replace "supra," with -- *supra,* --.
Line 42, Table 3, 3$^{rd}$ heading, replace "Regenertion" with -- Regeneration --.

Column 20,
Lines 21-22, replace "In Vivo" with -- *In Vivo* --.
Line 47, replace "Louie et al.," with -- Louie *et al.,* --.
Line 48, replace ", 1994;" with -- (1994); --.
Line 49, replace "Kinsman et al.," with -- Kinsman *et al.,* --.
Line 49, replace ", 1993;" with -- (1993); --.
Line 51, replace ", 1995;" with -- (1995); --.
Line 54, replace "J. Mycol. Med., 6 (Suppl. 1):7-10" with -- *J. Mycol. Med.,* 6 (*Suppl.* 1):7-10 --.

Column 21,
Line 2, replace "e.g., Aspergillus" with -- *e.g., Aspergillus* --.
Line 3, replace "Candida" with -- *Candida* --.
Lines 4, 7, 8 and 32, replace "e.g.," with -- *e.g.,* --.
Line 13, replace "In Vivo" with -- *In Vivo* --.
Line 19, replace "See, e.g.," with -- See, *e.g.,* --.
Line 19, replace "Andriole et al." with -- Andriole *et al.* --.
Line 20, replace "*Dis.,* b 14(Suppl." with -- *Dis.,* 14(*Suppl.* --.
Line 21, replace "Patterson et al.," with -- Patterson *et al.* --.
Lines 22-23, replace "George et al.," with -- George *et al.,* --.
Lines 44, 47 and 49, replace "Aspergillus" with -- *Aspergillus* --.
Line 45, replace "EUISA" with -- ELISA --.
Line 52, replace "Chilvers et al.," with -- Chilvers *et al.,* --.
Line 64, replace "In Vivo" with -- *In Vivo* --.

UNITED STATES PATENT AND TRADEMARK OFFICE
CERTIFICATE OF CORRECTION

PATENT NO. : 6,372,212 B1
DATED : April 16, 2002
INVENTOR(S) : Patrick W. Gray

It is certified that error appears in the above-identified patent and that said Letters Patent is hereby corrected as shown below:

Column 22,
Line 2, replace "Rouse et al.," with -- Rouse *et al.*, --.
Lines 6, 24 and 45, replace "Candida" with -- *Candida* --.
Lines 7 and 58, replace "e.g.," with -- *e.g.*, --.
Line 15, replace "Bayer et al.," with -- Bayer *et al.*, --.
Line 17, replace "5 x 108" with -- $5 \times 10^8$ --.
Line 40, replace "In Vivo" with -- *In Vivo* --.
Line 46, replace "Park et al.," with -- Park *et al.*, --.

Column 23,
Line 16, replace "Aspergillus" with -- *Aspergillus* --.
Line 17, replace "Jain et al.," with -- Jain *et al.*, --.
Line 30, replace "In Vivo" with -- *In Vivo* --.

Column 24,
Line 1, replace "*endocarditis*" with -- endocarditis --.
Line 3, replace "Longman et al.," with -- Longman *et al.*, --.
Line 3, replace "12(Suppl." with -- 12(*Suppl.* --.

Signed and Sealed this

Nineteenth Day of August, 2003

JAMES E. ROGAN
*Director of the United States Patent and Trademark Office*